US012564507B2

(12) United States Patent
Giuntoli et al.

(10) Patent No.: US 12,564,507 B2
(45) Date of Patent: Mar. 3, 2026

(54) WALKING BOOT, CHAFE ASSEMBLY, PROTECTIVE RIM FOR A PUSH-BUTTON RELEASE VALVE AND RELATED METHODS

(71) Applicant: DJO, LLC, Carlsbad, CA (US)

(72) Inventors: David M. Giuntoli, Carlsbad, CA (US); Ryan Held, Oceanside, CA (US); Paul Klock, Carlsbad, CA (US); Jeff Mullally, La Mesa, CA (US); Alexis Doty, Carlsbad, CA (US); Robert Bejarano, Carlsbad, CA (US)

(73) Assignee: DJO, LLC, Carlsbad, CA (US)

( * ) Notice: Subject to any disclaimer, the term of this patent is extended or adjusted under 35 U.S.C. 154(b) by 299 days.

(21) Appl. No.: 18/196,560

(22) Filed: May 12, 2023

(65) Prior Publication Data

US 2023/0355417 A1 Nov. 9, 2023

Related U.S. Application Data

(62) Division of application No. 16/865,937, filed on May 4, 2020, now Pat. No. 11,666,471.

(Continued)

(51) Int. Cl.
*A61F 5/01* (2006.01)
(52) U.S. Cl.
CPC ............ *A61F 5/0111* (2013.01); *A61F 5/012* (2013.01); *A61F 5/0195* (2013.01)
(58) Field of Classification Search
CPC .. A61F 5/00; A61F 5/01; A61F 5/0102; A61F 5/0104; A61F 5/0111; A61F 5/012;
(Continued)

(56) References Cited

U.S. PATENT DOCUMENTS 641,572 A * 1/1900 Arnsfield .................. A43B 7/06
36/3 R
3,099,870 A * 8/1963 Seeler .................. A62B 18/084
24/642

(Continued)

FOREIGN PATENT DOCUMENTS

CN 1293874 A 5/2001
CN 2902228 5/2007

(Continued)

OTHER PUBLICATIONS

International Search Report and Written Opinion cited in PCT/US2020/031314, dated Jul. 31, 2020.

(Continued)

*Primary Examiner* — Alireza Nia
*Assistant Examiner* — Gina McCarthy
(74) *Attorney, Agent, or Firm* — Veros Legal Solutions, LLP

(57) ABSTRACT

A walking brace is provided. The walking brace includes a U-shaped malleable stay configured to hold a manually-bent shape. The walking brace includes an integral portion. The integral portion includes a footbed, a first upright disposed at a first side of the footbed and a second upright disposed on a second side of the footbed. The integral portion is overmolded onto the U-shaped malleable stay such that the U-shaped malleable stay extends through each of the footbed, the first upright and the second upright. Other walking braces are provided wherein the integral portion includes a pocket configured to receive the U-shaped malleable stay at an underside of the integral portion such that the U-shaped malleable stay extends through each of the footbed, the first upright and the second upright. A method of manufacturing a walking brace is also provided.

17 Claims, 37 Drawing Sheets

200
210
2802
2606
2600
2704
2700

Related U.S. Application Data

(60) Provisional application No. 62/894,362, filed on Aug. 30, 2019, provisional application No. 62/885,690, filed on Aug. 12, 2019, provisional application No. 62/847,175, filed on May 13, 2019.

(58) Field of Classification Search
CPC ........ A61F 5/0127; A61F 5/0195; A61F 5/04; A61F 5/05; A61F 5/058; A61F 5/05841; A61F 5/0585; A43B 7/00; A43B 7/18; A43B 7/20
See application file for complete search history.

(56) References Cited

U.S. PATENT DOCUMENTS

| | | | | |
|---|---|---|---|---|
| 4,217,706 | A | * | 8/1980 | Vartanian .............. A61F 5/0195 |
| | | | | 36/110 |
| 4,771,768 | A | | 9/1988 | Crispin |
| 5,226,875 | A | * | 7/1993 | Johnson ................... A43B 7/20 |
| | | | | 36/114 |
| 5,286,431 | A | * | 2/1994 | Banfield ............ A44B 18/0076 |
| | | | | 264/274 |
| 6,155,998 | A | | 12/2000 | Gilmour |
| 6,383,156 | B1 | | 5/2002 | Enzerink et al. |
| 11,666,471 | B2 | | 6/2023 | Giuntoli et al. |
| 2003/0196352 | A1 | * | 10/2003 | Bledsoe ................. A43B 7/141 |
| | | | | 36/110 |
| 2004/0167453 | A1 | | 8/2004 | Peters |
| 2005/0085755 | A1 | | 4/2005 | Rabe |
| 2005/0131324 | A1 | | 6/2005 | Bledsoe |
| 2005/0172517 | A1 | | 8/2005 | Bledsoe et al. |
| 2006/0293624 | A1 | * | 12/2006 | Enzerink .............. A61F 5/0125 |
| | | | | 602/26 |
| 2007/0010770 | A1 | | 1/2007 | Gildersleeve |
| 2007/0293798 | A1 | * | 12/2007 | Hu ......................... A61F 5/0195 |
| | | | | 602/27 |
| 2009/0227927 | A1 | | 9/2009 | Frazer |
| 2009/0287127 | A1 | * | 11/2009 | Hu ......................... A61F 5/0111 |
| | | | | 602/27 |
| 2014/0197565 | A1 | | 7/2014 | Hu et al. |
| 2014/0197656 | A1 | | 7/2014 | Ochial et al. |
| 2014/0276301 | A1 | * | 9/2014 | Grim .................... A61F 5/0127 |
| | | | | 602/12 |
| 2017/0165095 | A1 | * | 6/2017 | Romo ................... A61F 5/0111 |

FOREIGN PATENT DOCUMENTS

| | | | |
|---|---|---|---|
| CN | 109154163 | A | 1/2019 |
| DE | 3622321 | A1 | 1/1988 |
| DE | 202018100539 | U1 | 3/2018 |
| EP | 2194938 | A2 | 6/2010 |
| JP | S50-002555 | | 2/1974 |
| JP | H02271804 | | 11/1990 |
| JP | 2002136304 | A | 5/2002 |
| JP | 2005296327 | A | 10/2005 |
| WO | 2020225385 | A1 | 11/2020 |

OTHER PUBLICATIONS

AU Examination Report No. 1, mailed May 13, 2022.
AU Examination Report No. 2, mailed Aug. 2, 2022.
CA Office Action, mailed Jan. 4, 2023.
CA Office Action, mailed Jul. 28, 2023.
Japan Intellectual Property Office Action, Jan. 24, 2023.
JP Office Action, Notice of Reason for Rejections, mailed Aug. 8, 2023.
Notice of Allowance mailed on Apr. 18, 2024 in CA 3137303.
Office Action mailed on Aug. 28, 2024 in CN 202080035497.4.

* cited by examiner

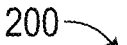
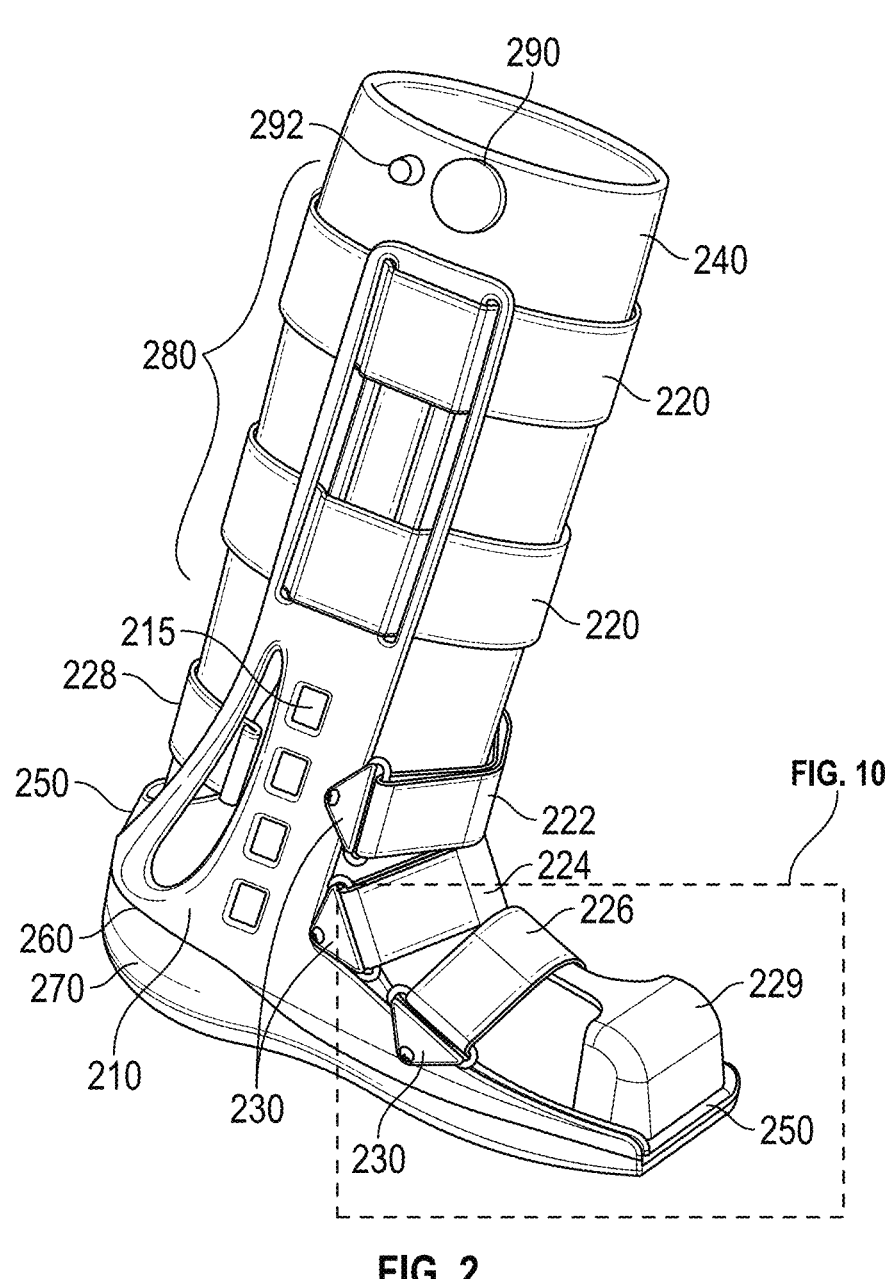
FIG. 2

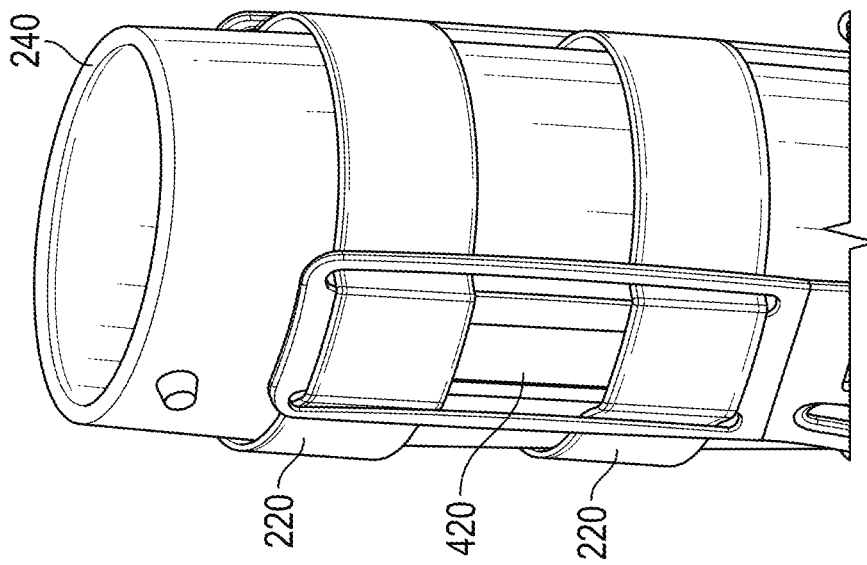
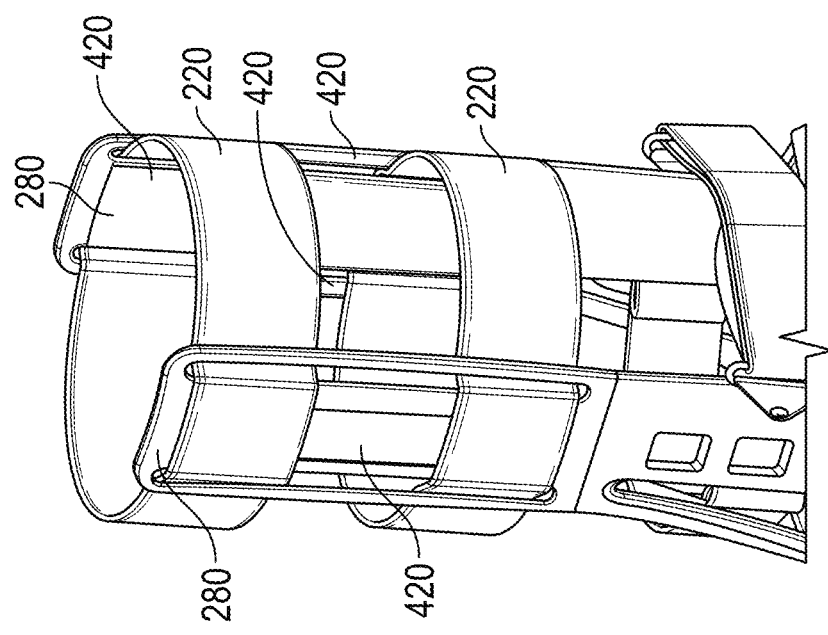
FIG. 4D

200

215

210

215a          215b

602

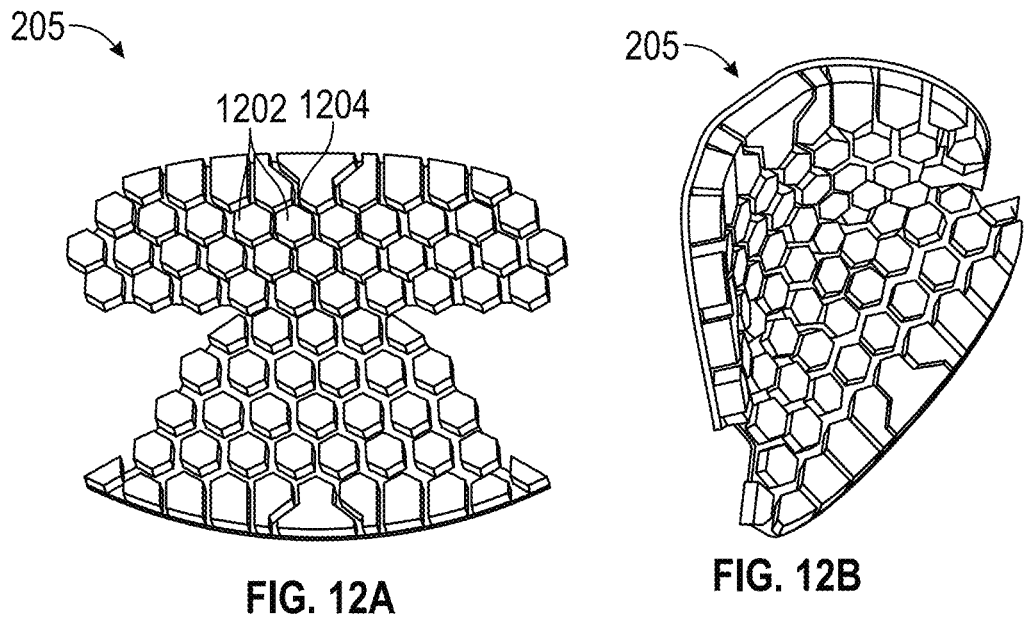
FIG. 12A                    FIG. 12B
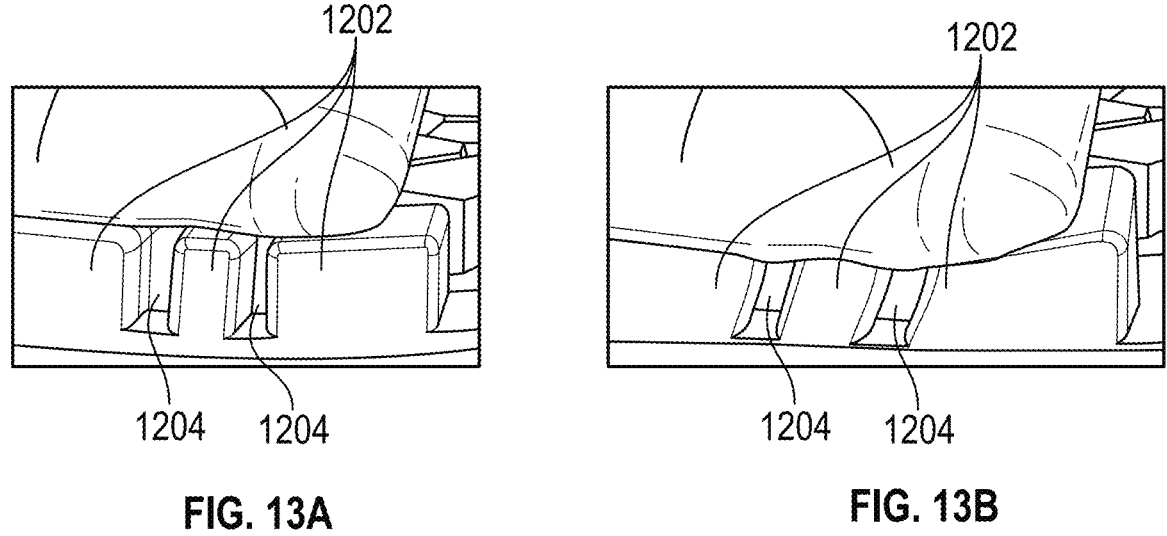
FIG. 13A                    FIG. 13B

1602

1602

200

2600

2604

2600

WALKING BOOT, CHAFE ASSEMBLY, PROTECTIVE RIM FOR A PUSH-BUTTON RELEASE VALVE AND RELATED METHODS

RELATED APPLICATIONS

This application is a divisional of U.S. application Ser. No. 16/865,937, filed on May 4, 2020, which claims priority to U.S. Provisional Application No. 62/847,175, filed on May 13, 2019, U.S. Provisional Application No. 62/885,690, filed on Aug. 12, 2019, and U.S. Provisional Application No. 62/894,362, filed on Aug. 30, 2019, the entire contents of each of which are hereby incorporated by reference.

FIELD OF THE INVENTION

In the field of orthopedic devices, the invention relates to an improved walking brace, improved rotatable chafes configurable to be secured into an upright portion of such a walking brace, and/or a protective rim and push-button release valve for inflating at least a portion of such a walking brace, as well as methods of using and/or manufacturing any of the same.

BACKGROUND

Walking boots generally use some type of strap(s) to secure the lower leg and foot into such a device. Common strap attachment to the boot itself can include a slot at the edge of the boot and/or boot upright where a strap can pass through, a rivet on a chafe, typically plastic, having means to snap into a feature with the boot's edge, generally a slot that does not allow rotation. Such strap attachments that do rotate fail to allow the strap to easily tighten onto the anatomy. The chafe doesn't flex, rotate, hinge and/or bend and, so, fail to properly tightly bind a narrow leg into such walking boots.

Accordingly, there is a need for improved walking boots which are durable, customizable, and can accommodate extra bulk such as bandages. In addition, there is a need for improved push-button release valves for inflating at least a portion of such a walking brace. Further, there is a need for improved rotatable, flexible, hinging and/or bendable chafes configurable to be secured into an upright portion of a walking brace.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

According to some embodiments, a walking brace is provided. The brace includes a U-shaped malleable stay configured to hold a manually-bent shape. The brace includes an integral portion. The integral portion includes a footbed, a first upright disposed at a first side of the footbed and a second upright disposed on a second side of the footbed. The integral portion is overmolded onto the U-shaped malleable stay such that the U-shaped malleable stay extends through each of the footbed, the first upright and the second upright.

According to some embodiments, a walking brace is provided. The brace includes a U-shaped malleable stay configured to hold a manually-bent shape. The brace includes an integral portion. The integral portion includes a footbed, a first upright disposed at a first side of the footbed, a second upright disposed on a second side of the footbed, and a pocket configured to receive the U-shaped malleable stay at an underside of the integral portion such that the U-shaped malleable stay extends underneath the footbed and through each of the first upright and the second upright.

According to some embodiments, a method of manufacturing a walking brace is provided. The method includes providing a U-shaped malleable stay that is configured to hold a manually-bent shape. The method includes overmolding an integral portion of the walking brace around the U-shaped malleable stay to form a footbed, a first upright disposed at a first side of the footbed and a second upright disposed on a second side of the footbed such that the U-shaped malleable stay extends through each of the footbed, the first upright and the second upright.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

FIG. 2 illustrates a perspective view of a walking brace, in accordance with some example embodiments;

FIG. 4D illustrates the fasteners of FIG. 4C securing a liner directly to the upright extension of FIG. 4C, in accordance with some example embodiments;

FIG. 12A illustrates a perspective view of at least part of a molded insole for a walking brace, in accordance with some example embodiments;

FIG. 12B illustrates a perspective view of the molded insole of FIG. 12A folded into a shape of a heel, in accordance with some embodiments;

FIG. 13A illustrates a magnified side view of the molded insole of FIG. 12A when little to no pressure is applied, in accordance with some embodiments;

FIG. 13B illustrates a magnified side view of the molded insole of FIG. 12A when significant pressure is applied, in accordance with some embodiments;

DETAILED DESCRIPTION

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Described herein is a walking brace (boot) having a wider foot bed for comfort and stability while still providing a relatively low profile. Also provided is a rocker bottom which helps to promote natural gait and to reduce plantar pressures. Cushioned inner and outer sole afford shock absorption and facilitate patient comfort during ambulation. A walking brace disclosed herein can be used in connection with a stress fracture of the lower leg, soft tissue injuries, stable fractures and injuries of the foot and ankle, bunionectomies, and metatarsal fractures, among other suitable uses. Moreover, a walking brace, according to at least some embodiments described herein, comprise uprights which can be manually bent to accommodate lower leg anatomy and bandages. For example, such a walking brace can include formable uprights which are advantageously constructed of plastic overmolded onto an aluminum stay.

Figure 1:
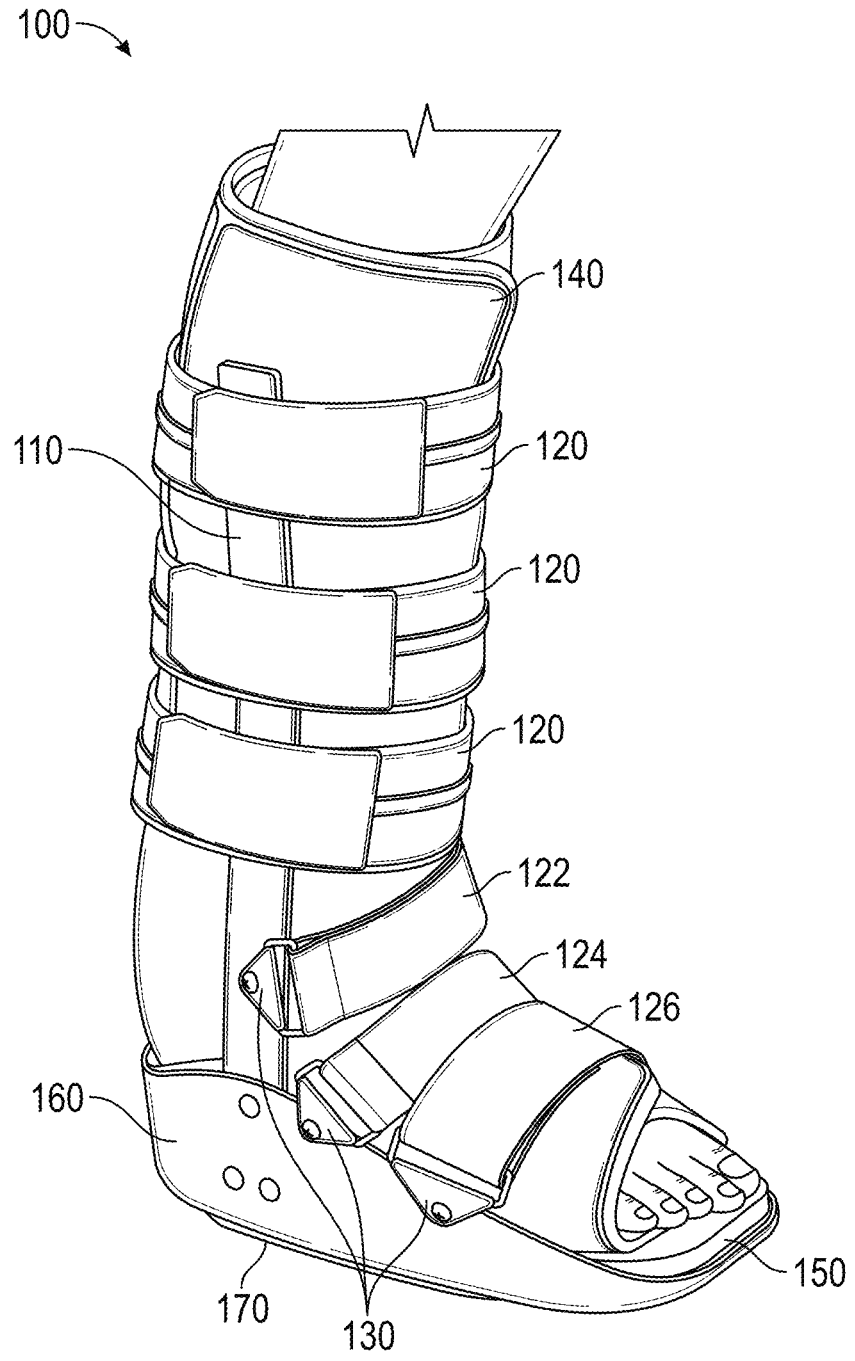
FIG. 1 illustrates a walking brace, in accordance with some example embodiments.

FIG. 1 illustrates a walking brace 100, in accordance with some example embodiments. Walking brace 100 is illustrated as having two aluminum uprights 110, a plurality of upright straps 120, a plurality of lower straps (including an ankle strap 122, a proximal strap 124, and a distal strap 126), a plurality of chafes 130, a liner 140, an insole 150, and a boot 160 having an under-boot sole 170. The remaining figures of this disclosure illustrate, describe and/or present one or more advancements over walking brace 100 of FIG. 1.

FIG. 2 illustrates a perspective view of a walking brace 200, in accordance with some example embodiments. Walking brace 200 is an advancement over walking brace 100 of FIG. 1. Walking brace 200 comprises a continuous plastic material that forms a footbed 260 as well as an upright 210 on either side of brace 200. In some embodiments, this continuous plastic material is overmolded onto a flexible aluminum stay 215. Such a one-piece, continuous plastic overmold eliminates the need for typical riveting of formable aluminum upright bars to a rigid plastic boot foot-bed.

In some embodiments, metallic stay 215 comprises a single, U-shaped aluminum stay configured to hold its bent form. In such embodiments, metallic stay 215 is continuous from the left to the right side. In some embodiments, such a "U" shaped aluminum stay can be insert-molded into boot footbed 260 at the time of manufacture and/or assembly. In some alternative embodiments, such a "U" shaped stay can be installed after boot 200 is molded, as illustrated in more detail in connection with FIGS. 7A-7C. In some other embodiments, stay 215 may comprise two "L" shaped aluminum pieces 215a, 215b that face one another, are substantially mirror-versions of one another, that can have a gap disposed between one another, and that are configured to form a substantial "U" shape, as will be described in more detail in connection with FIG. 6.

The formability of uprights 210 by manual application of force to bend uprights 210 is a boon to walking brace 200. In application, one has to balance between uprights 210 having sufficient stiffness to resist walking forces applied to brace 200 and uprights 210 being sufficiently malleable to bend and/or deform sufficiently to accommodate lower leg bandaging. Integration of metallic stay(s) 215 with footbed 260 and uprights 210 allows walking forces on boot 200 to be shared by the plastic of uprights 210 and metallic stay(s) 215.

Figure 3A:
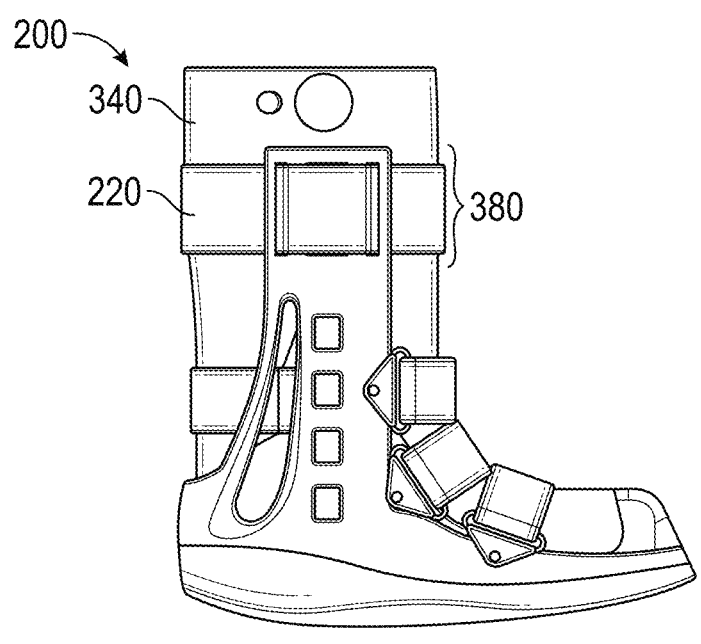
FIG. 3A illustrates a side view of a short walking brace, in accordance with some example embodiments.
Figure 3B:
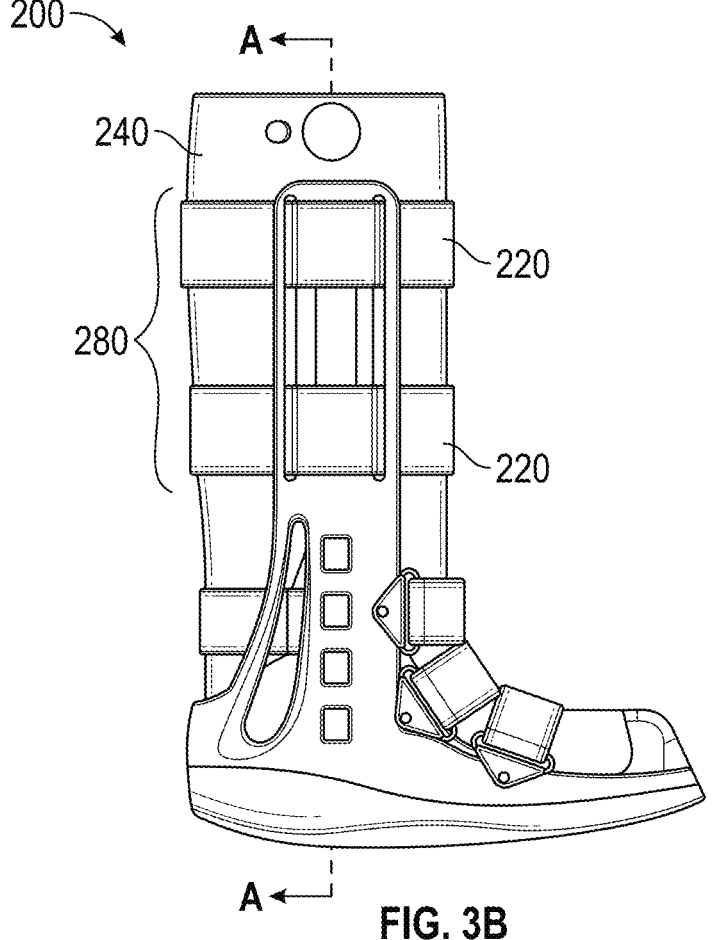
FIG. 3B illustrates a side view of a tall walking brace compared to the walking brace of FIG. 3A, in accordance with some example embodiments.
Figures 3C, 3D:
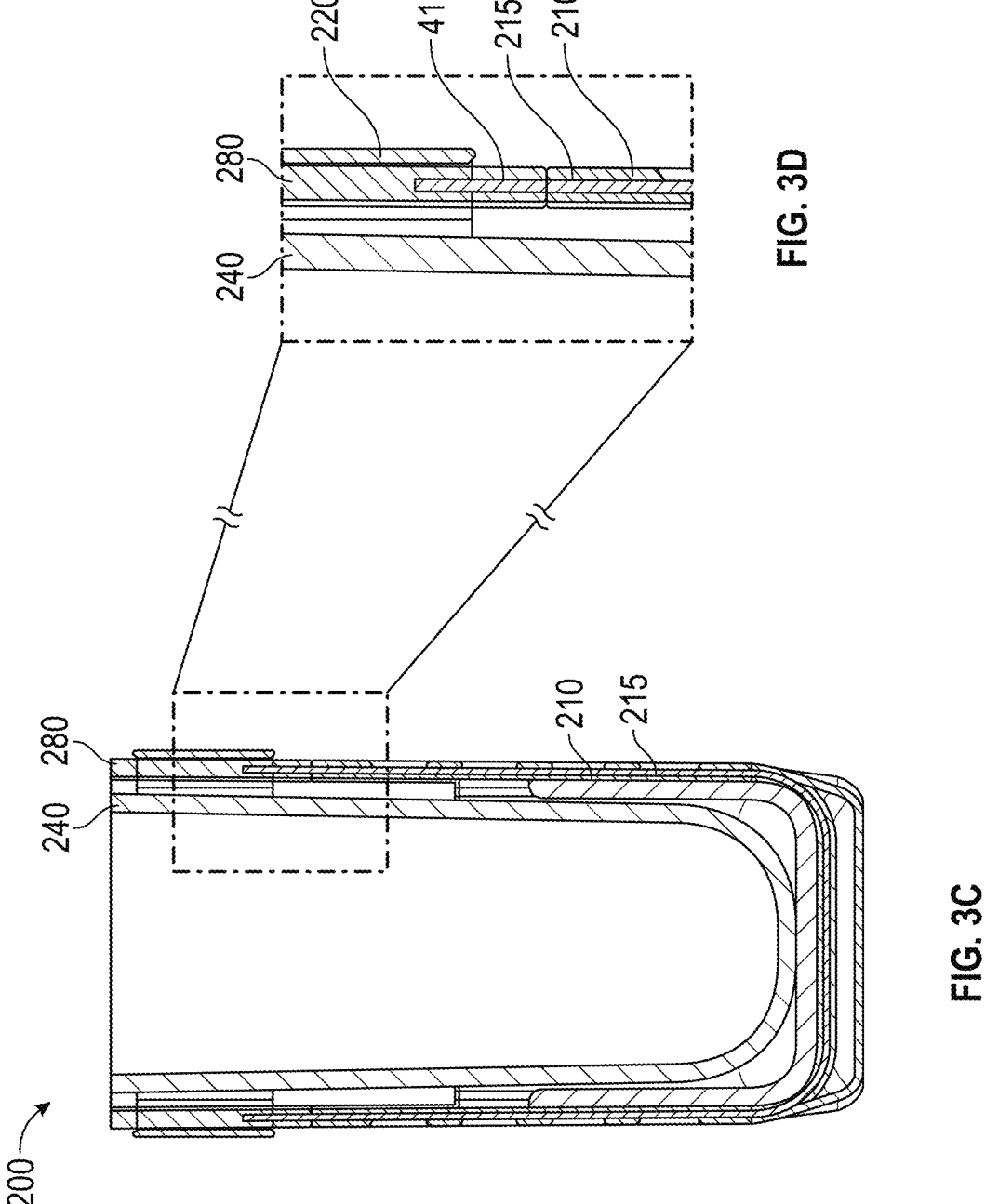
FIG. 3C illustrates a cutaway view of the brace of FIG. 3B along the cutline A-A' in FIG. 3B, in accordance with some example embodiments.
FIG. 3D illustrates a magnified view of the portion of the brace of FIG. 3C bounded by the dotted rectangular box, in accordance with some example embodiments.

The height, length and/or size of an interchangeable upright extension(s) 280, one-way snapped into a top of upright(s) 210, at least partially determine a height of walking brace 200. Advantageously, walking brace 200 can include a plurality of such extensions 280, each of which vary in height according to a desired brace size. These sizes can include extra small (XS), small (S), medium (M), large (L) and extra-large (XL), each associated with and/or having a corresponding predetermined height, length and/or size. For example, FIG. 3A illustrates a side view of a short version of walking brace 200 that utilizes a shorter interchangeable upright extension 380 compared to the larger interchangeable upright extension 280 shown in FIGS. 2 and 3B. FIG. 3B also includes a cutaway plane A-A', which illustrates metallic stay 215, among other features, in more detail in FIGS. 3C and 3D.

Turning back to FIG. 2, walking brace 200 comprises at least one upright strap 220, configured to secure a lower leg of a user into brace 200. Upright strap(s) 220 can couple to and/or be threaded through at least a portion of upright extension(s) 280,380. For example, in some embodiments that utilize shorter upright extension 380, as illustrated in at least FIG. 3A, only one upright strap 220 is coupled and/or threaded through at least a portion of shorter upright extension 380. In some other embodiments that utilize longer upright extension 280, as illustrated in at least FIGS. 2 and 3B, two or more upright straps 220 can be coupled and/or threaded through at least a portion of longer upright extension 280. However, the present disclosure is not so limited and any number of upright straps 220 can be utilized with any-sized upright extension described herein.

Brace 200 further includes a plurality of lower straps, for example, including an ankle strap 222 configured to wrap at least partly around and/or against an ankle of the user. In some embodiments, the plurality of lower straps includes a proximal foot strap 224 configured to wrap at least partly around and/or against a proximal portion of the foot of the user. In some embodiments, the plurality of lower straps includes a distal foot strap 226 configured to wrap at least partly around and/or against a portion of the foot of the user distal to the proximal portion discussed above.

In some embodiments, one or more of straps 222, 224, 226 are configured to couple to a respective one of a plurality of chafes 230, which are each configured to rotatably and/or flexibly secure one side of the respective strap to brace 200. Chafes 230 will be described in more detail in connection with at least FIGS. 25-30C below.

In some embodiments, brace 200 further includes a toe cover 229 configured to cover at least one toe of the user. Examples of toe cover 229 will be described in more detail in connection with at least FIGS. 10 and 11, which illustrate a magnified view of toe cover 229 within the dotted rectangular box of FIG. 2.

Figure 16A:
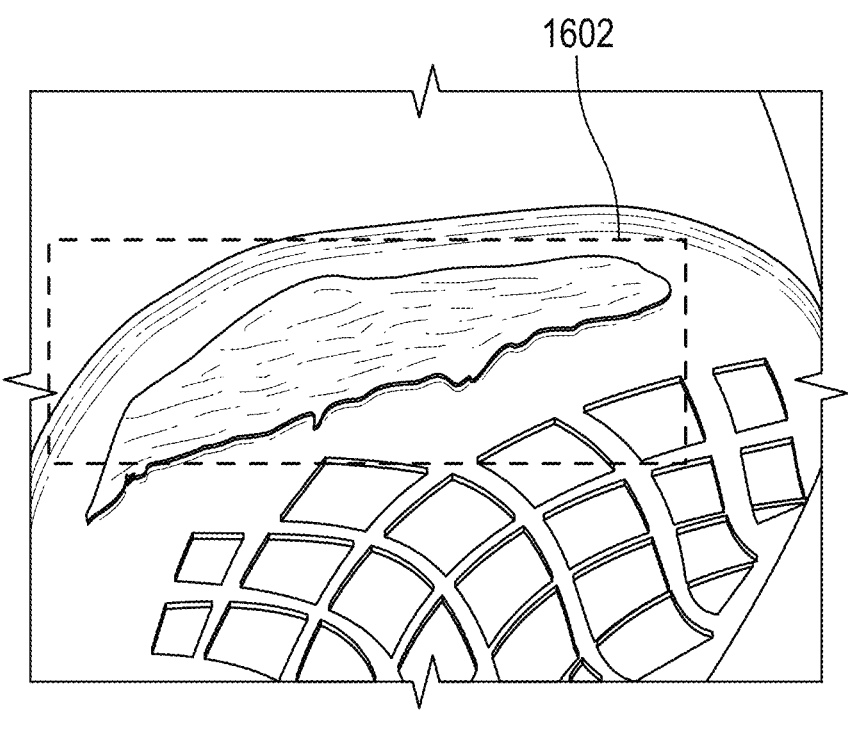
FIGS. 16A and 16B illustrate wear patterns and impact damage to an undersole of a walking brace, in accordance with some example embodiments.
Figure 16B:
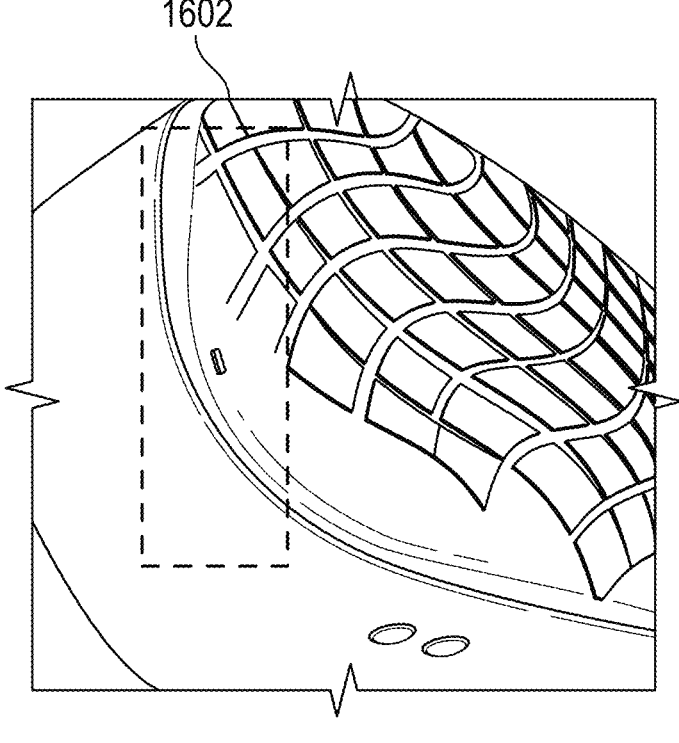

Brace 200 may further comprise an insole 250 disposed and configured to extend along a length of a top surface of footbed 260. Brace 200 may further comprise an under-boot sole 270. Examples of under-boot sole 270 will be described in more detail in connection with at least FIGS. 16A-17.

Brace 200 may further comprise a liner 240 comprising a soft, absorbent and, in some case, breathable, material configured to support and/or pad a foot and lower leg of a user. In some embodiments, liner 240 has an air pump 290, a pressure-release valve 292, and one or more air-tight, inflatable cavities (not shown in FIG. 2) disposed therein such that a desired amount of pressure and/or support can be provided to one or more physical locations of the users foot and/or lower leg associated with each of the one or more inflatable cavities.

In some embodiments, a height of liner 240 and/or of its similar versions can depend and/or be selected based at least in part on the height of brace 200 and/or a height of upright extensions 280. For example, FIG. 3A illustrates a liner 340 as having a first height, as utilized with brace 200 having shorter upright extensions 380, while FIG. 3B illustrates liner 240 having a second height greater than the first height, as utilized with brace 200 having longer upright extension 280. Further examples, aspects and/or advantages of one or more of liner 240, air pump 290, pressure-release valve 292 and/or the inflatable cavities are described in more detail in connection with at least FIGS. 18A-23C below.

Figure 4A:
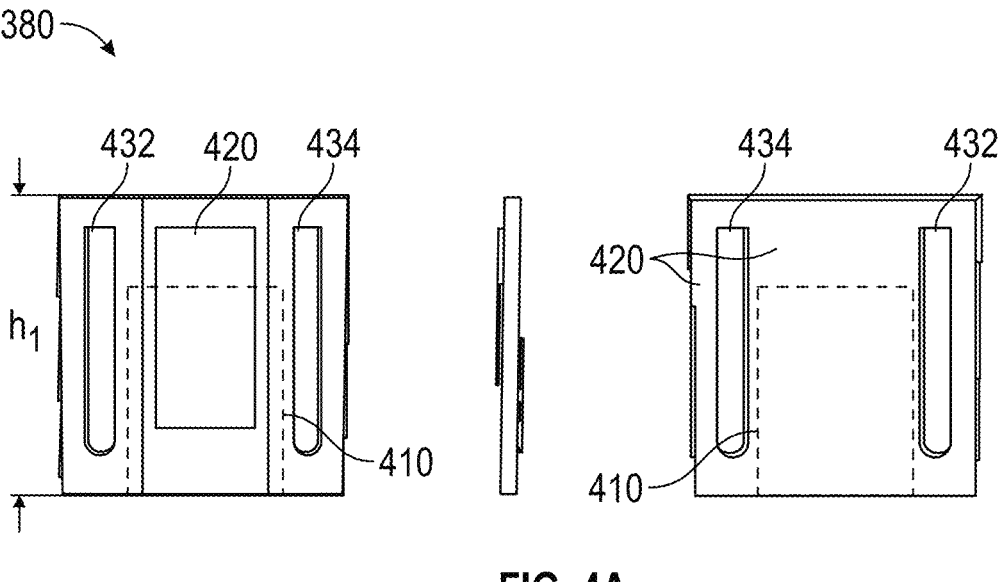
FIG. 4A illustrates front, side and back views of a taller upright extension for embodiments of a tall walking brace, in accordance with some embodiments.
Figure 4B:
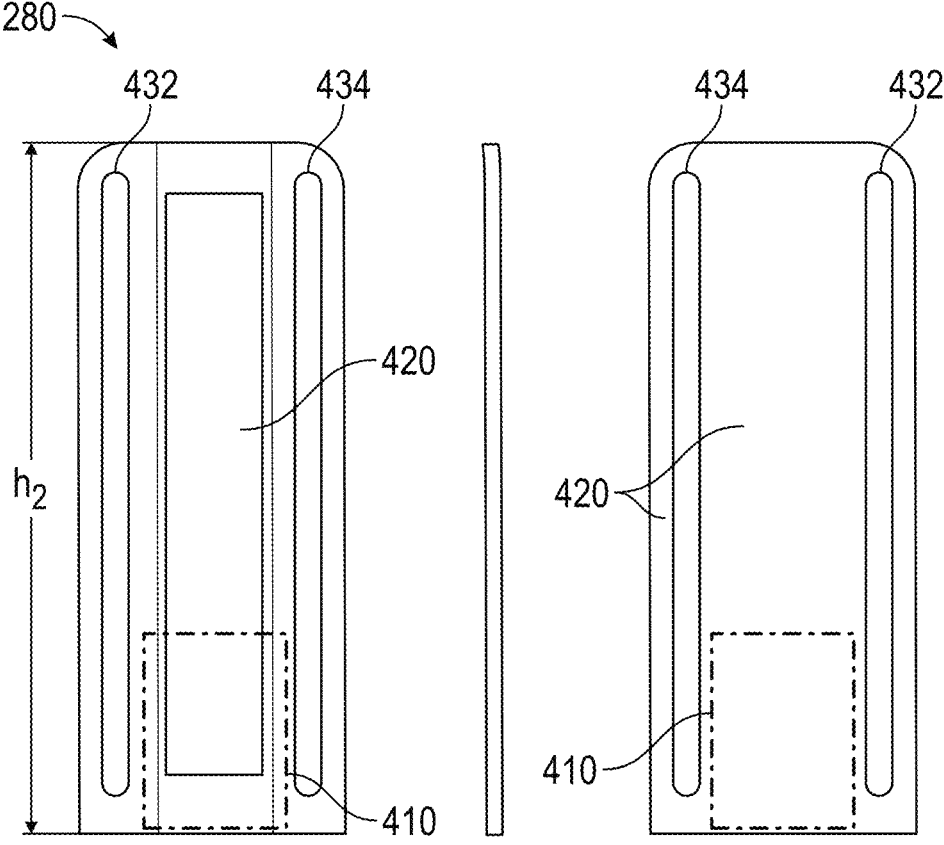
FIG. 4B illustrates front, side and back views of a shorter upright extension for embodiments of a short walking brace, in accordance with some embodiments.

Discussion will now turn to several aspects of upright extension(s) 280, 380. FIGS. 4A and 4B illustrate embodiments where strap fasteners 420 are disposed on inward- and outward-facing surfaces of upright extensions 380, 280 respectively, according to some embodiments. For example, each of upright extensions 280, 380 can comprise a first slot 432 disposed along one edge of upright extensions 280, 380 and a second slot 434 disposed along an opposite edge of upright extensions 280, 380. Each of first and second slots 432, 434 are configured to receive one or more of upright straps 220 and, thereby allow straps 220 to move up and/or down for proper user support and/or comfort.

In addition, each of upright extensions 280, 380 include a stay pocket 410 configured to receive an end portion of metallic stay 215 from the pocket's bottom end, as previously described in connection with at least FIG. 2. In some embodiments, a one-way snap feature is further contemplated at a bottom end of either of upright extensions 280, 380 to further secure metallic stay 215 within pocket 410. Having metallic stay 215 continue into upright extension 280, 380 stiffens the joint between upright extension 280, 380 and the lower portion of uprights 210.

As illustrated by FIGS. 4A, 4B, hook-type (or, e.g., complementary loop-type) fasteners 420 can be disposed on one or both of inward- (liner-facing) or outward-facing surfaces of upright extensions 280, 380. Fasteners 420 are configured to hold strap(s) 220 in place on upright extensions 280, 380. In some embodiments, fasteners may be Velcro-like. However, the present disclosure is not so limited and fasteners 420 can comprise any suitable type of fastener(s). In some embodiments, fastener 420 is disposed on a portion of the outward-facing side of upright extensions 280, 380 medial to first and second slots 432, 434. In some embodiments, fastener 420 is also and/or alternatively disposed on substantially all of the inward-facing side of upright extensions 280, 380, including the outer portions of first and second slots 432, 434.

Figure 4C:
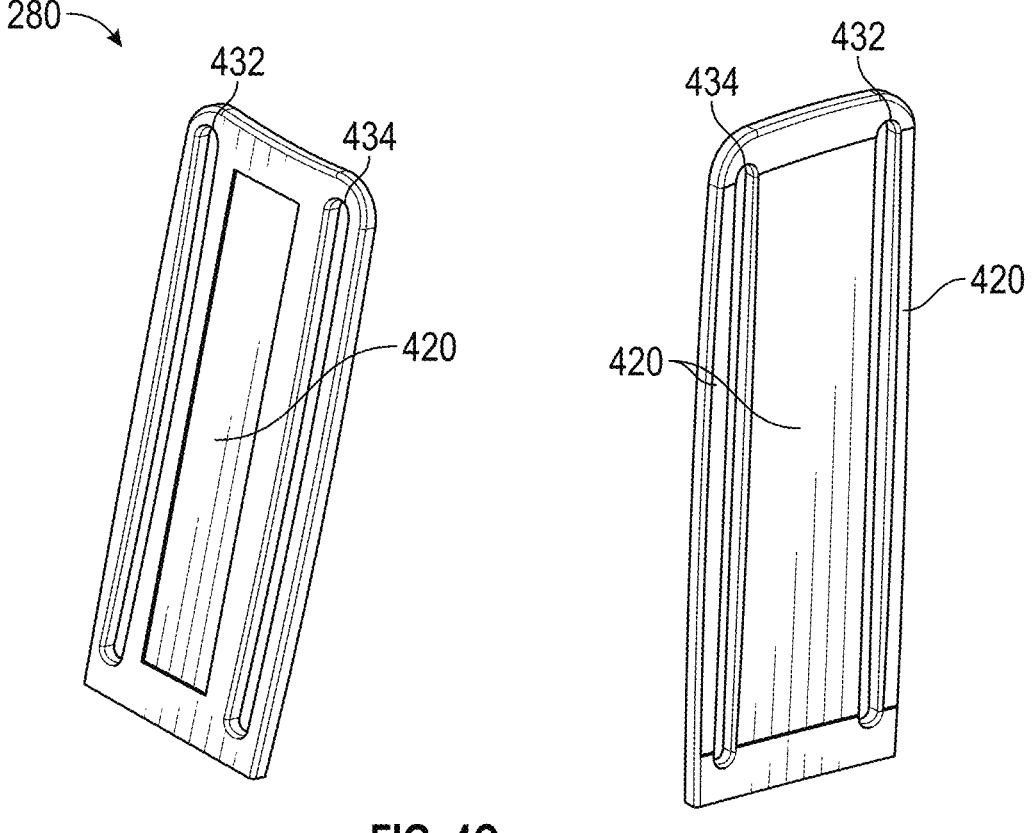
FIG. 4C illustrates fasteners molded into an upright extension, in accordance with some example embodiments.

In some embodiments, for example, as illustrated by FIGS. 4C and 4D, fasteners 420 can be molded into upright extensions 280, 380, rather than being merely disposed on a surface of upright extensions 280, 380. In such embodiments, upright extensions 280, 380 can be substantially as described in connection with FIGS. 4A and 4B, except that fasteners 420 molded into the inward-facing side of upright extensions 280, 380 can cover substantially all of the inward-facing side that extends between the top and bottom edges of first and second slots 432, 434.

In some embodiments, fasteners 420 disposed on inward-facing side of upright extensions 280, 380 can be configured to not only help hold straps 220 in place on upright extensions 280, 380 but also directly fasten liner 240 to upright extensions 280, 380, as illustrated in at least FIG. 4D.

Turning back to FIGS. 3C and 3D, FIG. 3C illustrates a cutaway view of brace 200 as taken along the cutline A-A' in FIG. 3B, while FIG. 3D illustrates a magnified view of the portion of FIG. 3C bounded by the dotted rectangular box, according to some embodiments. U-shaped metallic stay 215 is illustrated as being disposed at least partially within upright 210. At least a terminal portion of metallic stay 215 is illustrated as extending beyond the end of upright 210 such that the terminal portion is configured to slip into and couple within pocket 410 of upright extension(s) 280, 380. The magnified view of FIG. 3D further illustrates at least one upright strap 220 disposed at least along an outward-facing surface of upright extension 280, 380.

Figure 5:
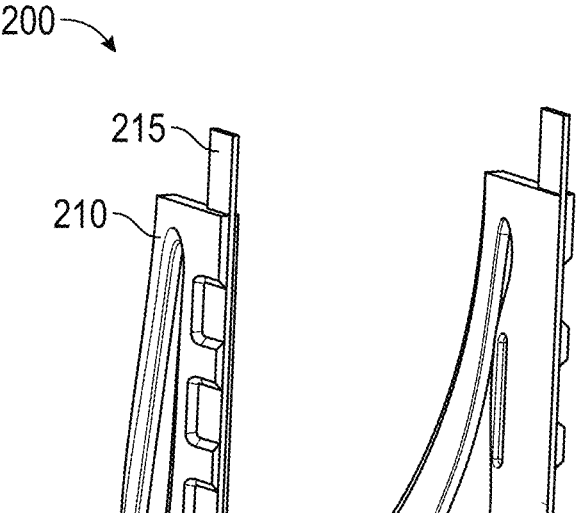
FIG. 5 illustrates a perspective cutaway view of at least a portion of brace uprights utilizing a single internal U-shaped metallic stay, in accordance with some example embodiments.
Figure 6:
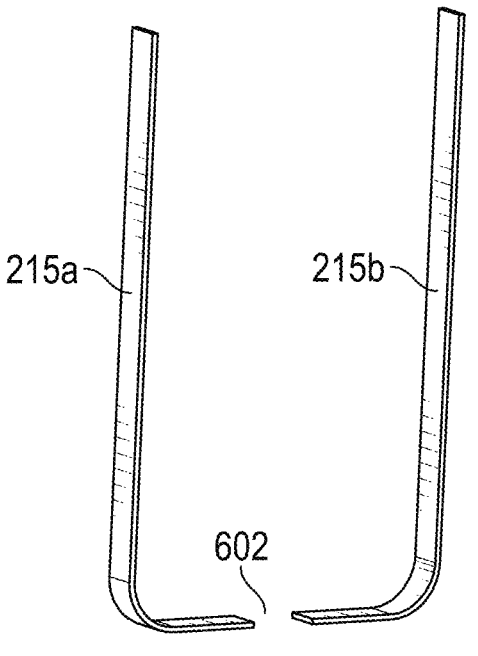
FIG. 6 illustrates a perspective view of an alternative mirrored pair of L-shaped metallic stays for similar utilization within brace uprights, in accordance with some example embodiments.

Turning to FIGS. 5 and 6, FIG. 5 illustrates a perspective cutaway view of at least a portion of uprights 210 utilizing a single U-shaped metallic stay 215, while FIG. 6 illustrates a perspective view of an alternative mirrored pair of L-shaped metallic stays 215a, 215b for similar utilization within uprights 210, in accordance with some example embodiments. As previously described in connection with at least FIG. 2, FIG. 5 shows use of a single U-shaped metallic stay 215 embedded or after-inserted into brace 200, specifically into at least a portion of uprights 210 and such that at least a terminal portion at each end of U-shaped metallic stay 215 projects beyond the ends of uprights 210. As an alternative to single U-shaped metallic stay 215, FIG. 6 shows use of a mirrored pair of L-shaped metallic stay 215a, 215b configured to be embedded or after-inserted into brace 200, specifically into at least respective portions of uprights 210 and also such that at least a terminal portion at of each of L-shaped metallic stay 215a, 215b projects beyond the ends of uprights 210. In some such embodiments, a lateral gap 602 is formed between the ends of L-shaped metallic stays 215a, 215b opposite to the above-described terminal portions. In some embodiments, a width of U-shaped metallic stay 215 and/or of L-shaped metallic stays 215a, 215b may gradually decrease toward a top end of the stay(s). Such a gradual decrease in width may, in some cases, reduce an amount of stress exerted on plastic portions of uprights 210 and/or upright extensions 280.

Figure 7A:
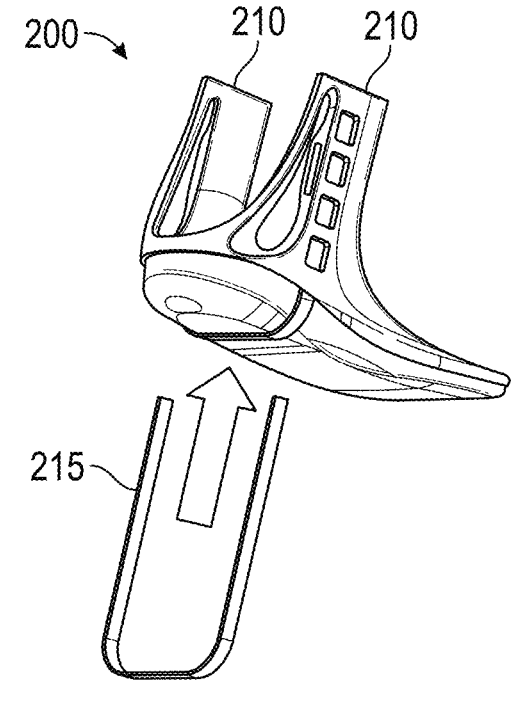
FIGS. 7A-7C illustrate an example for installing metallic stays into a pre-molded portion of a walking brace, in accordance with some example embodiments.
Figure 7B:
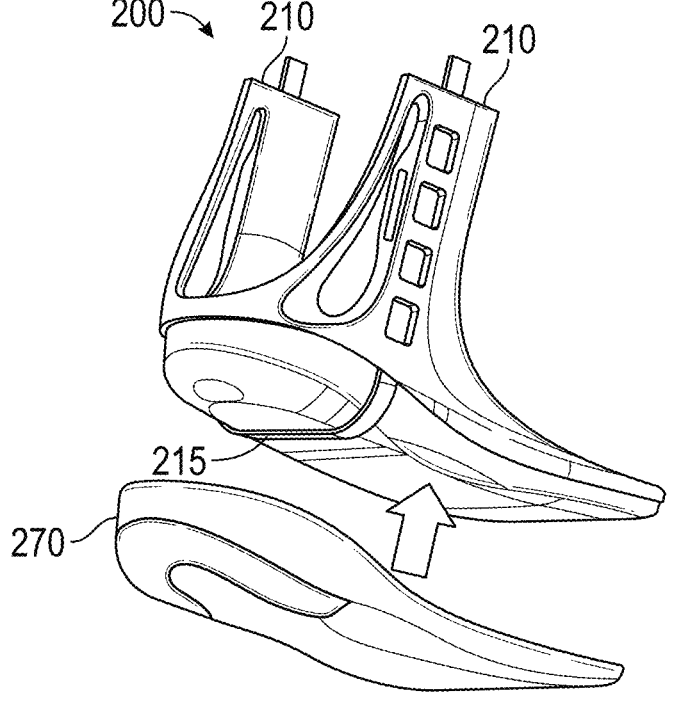
Figure 7C:
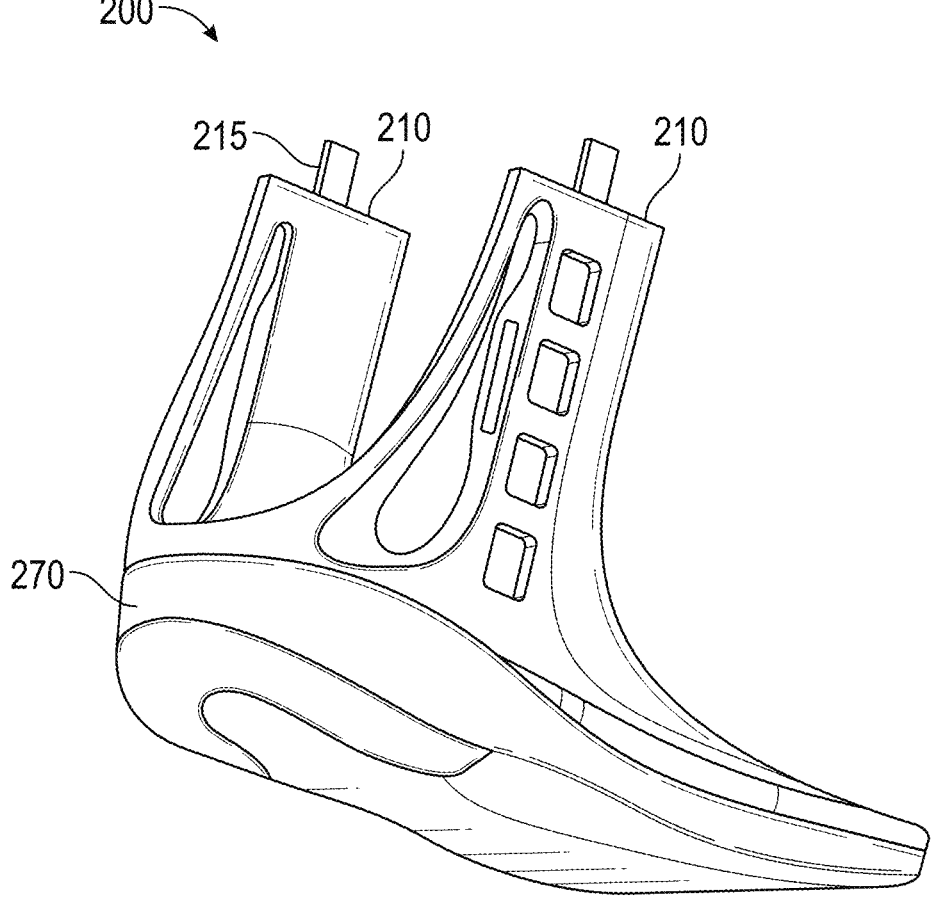

FIGS. 7A-7C illustrate several steps of a method of installing single U-shaped metallic stay 215 or mirror-paired L-shaped metallic stays 215a, 215b into at least a pre-molded portion of brace 200, in accordance with some example embodiments. For example, as illustrated in FIG. 7A, single U-shaped stay 215 can be slid into a pocket disposed in an underside of a pre-molded portion of brace 200 that includes at least uprights 210. Mirror-paired L-shaped metallic stays 215a, 215b could also be slid into the same or a similarly-shaped pocket. Once metallic stay(s) 215 or 215a, 215b are properly disposed within pre-molded portion of brace 200, under-boot sole 270 is bonded to the underside of the pre-molded portion of brace 200 and metallic stay(s) 215 or 215a, 215b, as illustrated by FIG. 7B, thereby securing metallic stay(s) 215 or 215a, 215b in place as illustrated by FIG. 7C.

Figure 8:
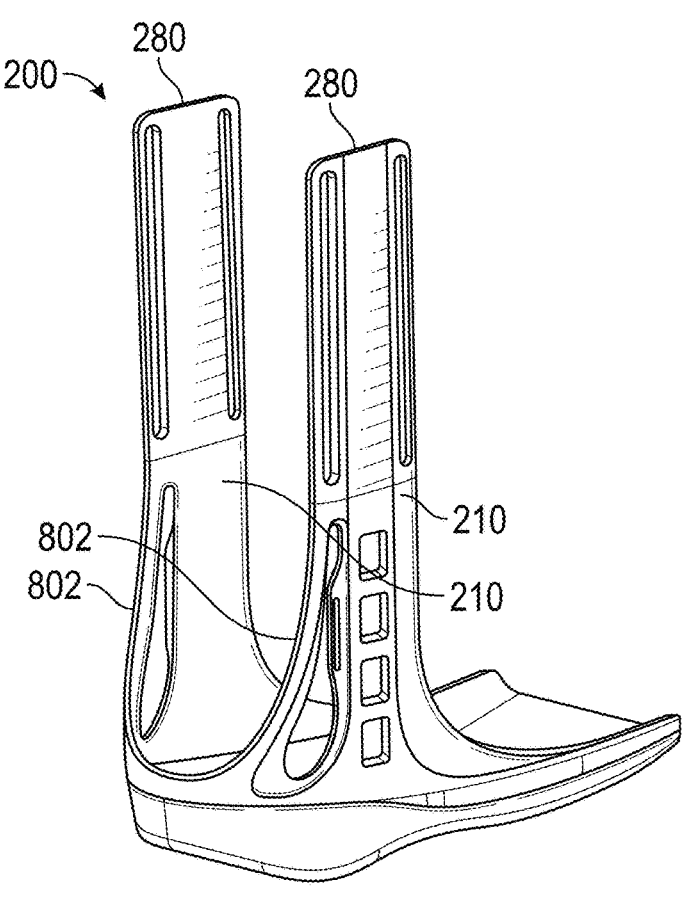
FIG. 8 illustrates a perspective view of gussets for providing added forward support to uprights of a walking brace, in accordance with some embodiments.
Figure 9:
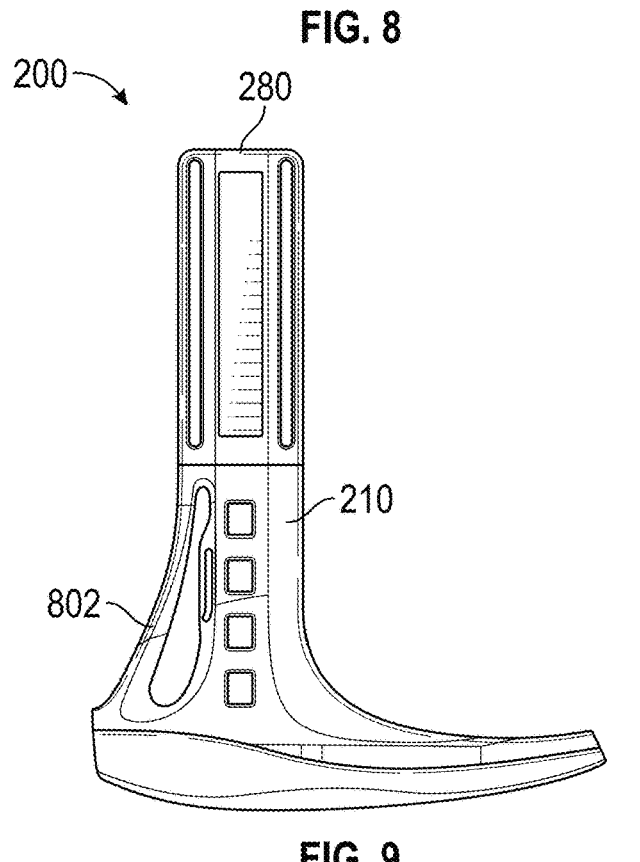
FIG. 9 illustrates a side view of the gussets of FIG. 8, in accordance with some embodiments.

Turning to FIGS. 8 and 9, uprights 210 are designed to be formable in the lateral direction but, to support a walking load, uprights 210 should also be rigid in the forward/aft direction. To achieve the desired lateral formability and forward stiffness, a rear gusset 802 can be molded into, onto, along, and/or as a part of each upright 210. Rear gussets 802 add forward support to uprights 210. In some embodiments, each gusset 802 extends at an angle from an upper portion of the upright 210, adjacent to upright extension 280, 380, to a bottom, posterior edge or portion of upright 210 adjacent to under-boot sole 270. For example, as shown in at least FIGS. 8 and 9, gussets 802 can form a substantially triangular shape or arrangement with uprights 210.

The above-described arrangement allows gussets 802 to bend in a lateral direction along with uprights 210 when uprights 210 are bent in an outward, lateral direction as needed to accommodate the fit of the user. However, walking imposes forces on brace 200, for example, on uprights 210 and/or upright extensions 280, 380 that cause tension and/or compression along the direction of extension of gussets 802. In this way, suitable stiffness of uprights 210 in the forward/aft direction are achieved.

Figure 10:
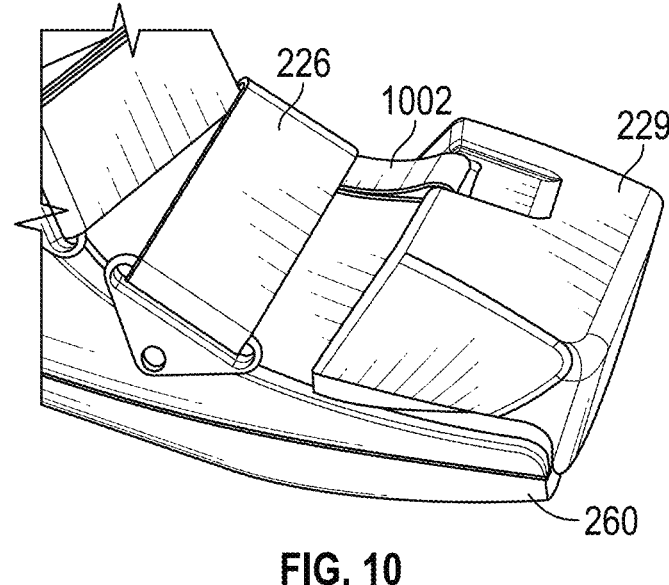
FIG. 10 illustrates a magnified perspective view of a toe cover for a walking brace, in accordance with some example embodiments.
Figure 11:
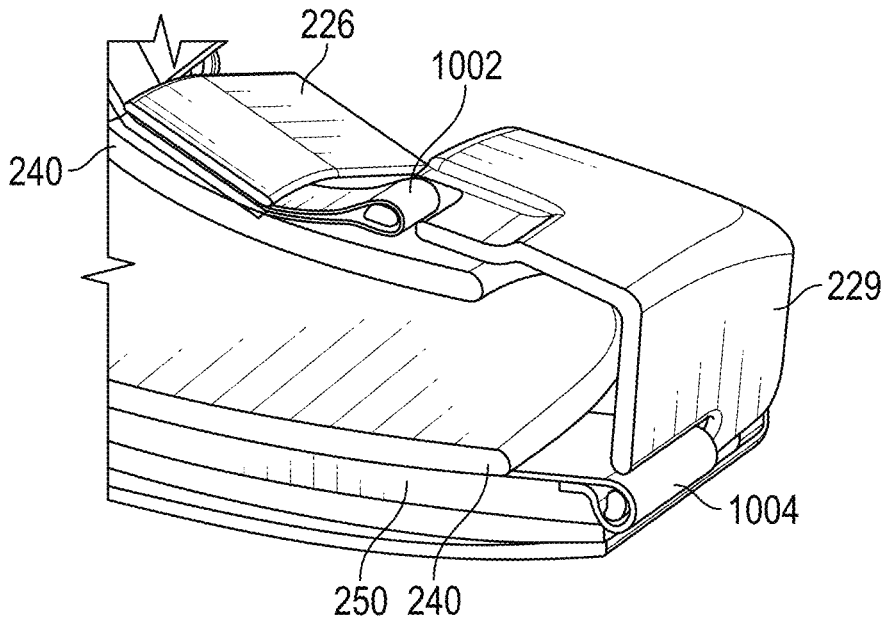
FIG. 11 illustrates a magnified perspective cutaway view of the toe cover of FIG. 10, in accordance with some example embodiments.

Discussion now turns to FIGS. 10 and 11, which illustrate magnified perspective and cutaway views of protective toe cover 229 of walking brace 200. Toe cover 229 is advantageously constructed from hard molded plastic. However, the present disclosure is not so limited and cover 229 can comprise any suitable material, including but not limited to rubber. In some embodiments, toe cover 229 is removable from brace 200. Toe cover 229 can be secured in place utilizing one or more straps, for example hook and loop straps. A first toe cover strap 1002 can couple at least a top portion of toe cover 229 to one or both of distal strap 226 and liner 240. A second toe cover strap 1004 can couple at least a forward portion of toe cover 229 to one or both of insole 250 and an underside of liner 240. In some embodiments, utilization of first toe cover strap 1002 without second toe cover strap 1004 allows toe cover 229 to be removable and follow distal strap 226 when it is released. However, toe cover may still be removable utilizing both first and second toe cover straps 1002, 1004. While slightly less secure than an arrangement utilizing both first and second toe cover straps 1002, 1004, such a one toe cover strap arrangement provides a potentially simpler entry and exit to toe cover 229.

Discussion now turns to insole 205 of FIG. 2. In some embodiments, insole 205 can be injection molded, compression molded, or cast into an initial and/or final shape. In some embodiments, insole 205 is made of foam. However, the present disclosure is not so limited and insole 205 can be constructed of any suitable material, for example and not limitation, a rubber-like material. In some embodiments, insole 205 can include air channels, as shown and described in connection with at least FIGS. 12A-13B.

An issue with body padding, in general, is trapped heat next to the skin. Perforations through the padding can help vent trapped heat, but this technique only works where the perforations span from the skin to ambient air. When there is a solid structure behind the padding preventing a direct air ventilation, conventional insoles can become warm to the wearer. Accordingly, one aspect of the present disclosure, comprises an insole having a waffle-like pattern of raised portions and venting channels disposed therebetween, allowing comfortable support to a foot of the user while also providing air ventilation along the channels even where conventional padding perforations would be presented with an impervious barrier to air ventilation by other, substantially solid portions of a brace.

FIGS. 12A-13B illustrate various perspective and side views of at least part of a molded insole for a walking brace, in accordance with some example embodiments. In some embodiments, the insole illustrated in FIGS. 12A-13B is at least a portion of insole 205 of walking brace 200. In some embodiments, as illustrated in FIG. 12A, insole 205 is a substantially flat, molded insole comprising a plurality of raised portions 1202 separated from one another by a plurality of air channels 1204. FIG. 12B illustrates the portion of insole 205 of FIG. 12A folded, molded and/or otherwise bent into a shape configured to support a heel of the user. In some other embodiments, insole 205 can be molded directly into a desired shape, rather than being folded or otherwise bent into its final shape.

FIG. 13A illustrates a side view of insole 205 of FIGS. 12A and 12B having little or no applied pressure, while FIG. 13B illustrates a side view of insole 205 having substantial applied pressure, in accordance with some example embodiments. As illustrated in FIG. 13A, when little or no pressure is applied to insole 205, raised portions 1202 and air channels 1204 are in their resting, undistorted shapes. However, applying substantial pressure to insole 205 causes raised portions 1202 and air channels 1204 to distort from their resting shapes, as shown in FIG. 13B. This compression and release of insole 205 by a foot of the user forces air through channels 1204 and this exchanges humid and hot air, created by the body, with ambient air, thereby cooling the padding skin regions.

Figure 14A:
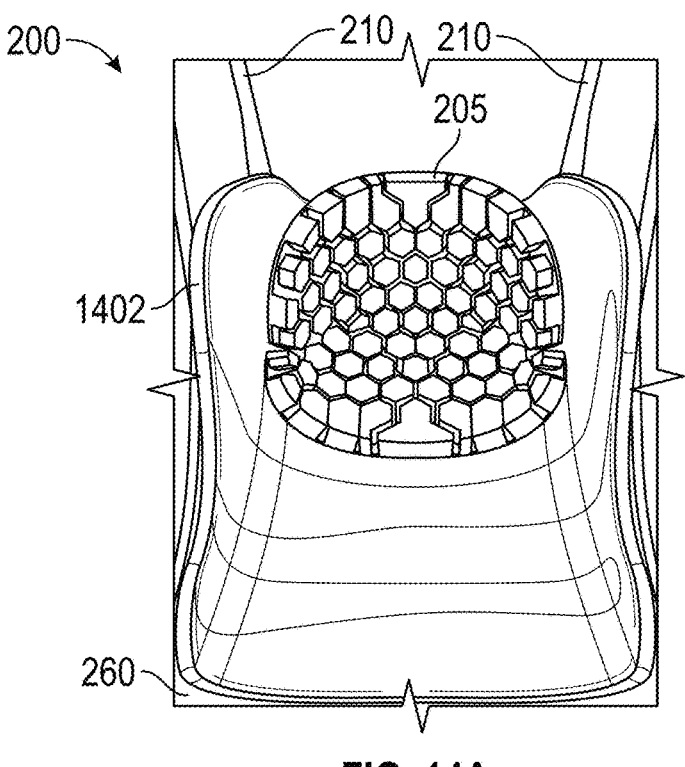
FIG. 14A illustrates a front view of a molded insole disposed within at least a portion of a walking brace, in accordance with some example embodiments.
Figure 14B:
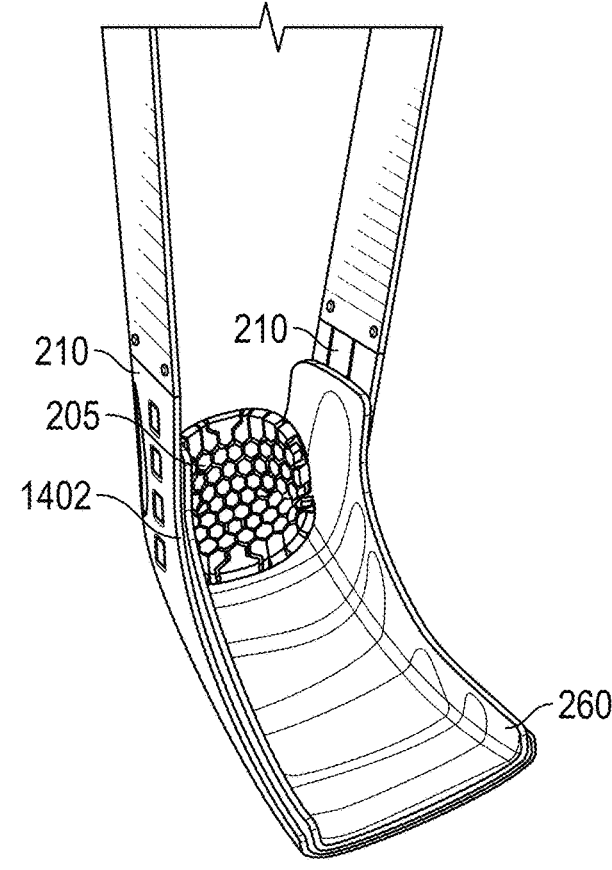
FIG. 14B illustrates a perspective view of the molded insole of FIG. 14A, in accordance with some example embodiments.

FIGS. 14A and 14B illustrate respective front and perspective views of the heel section of insole 205 (as previously described in connection with FIGS. 12A-13B) disposed within a pre-molded portion of brace 200, between uprights 210 and over footbed 206. Advantageously, insole 205 is configured to cover an entire area shown by the thick line 1402 in FIGS. 14A and 14B. In some embodiments, insole 205 is adhered or snapped into the pre-molded portion of brace 200 as shown to secure insole 205 in place.

Figure 15A:
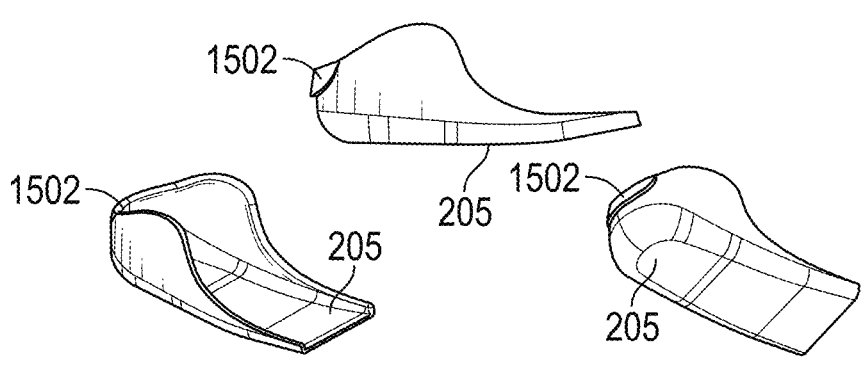
FIGS. 15A-15D illustrate an example for installing a molded insole into a walking brace, in accordance with some example embodiments.
Figure 15B:
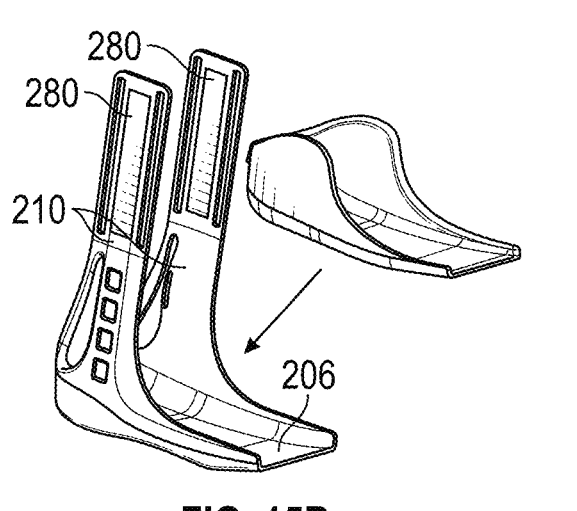
Figure 15C:
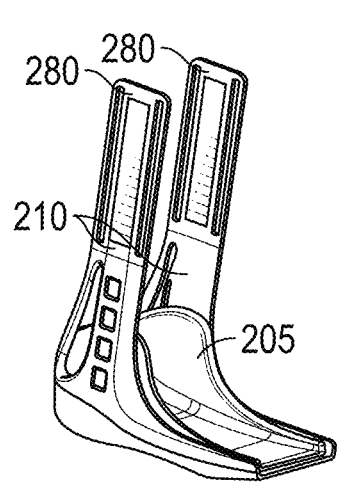
Figure 15D:
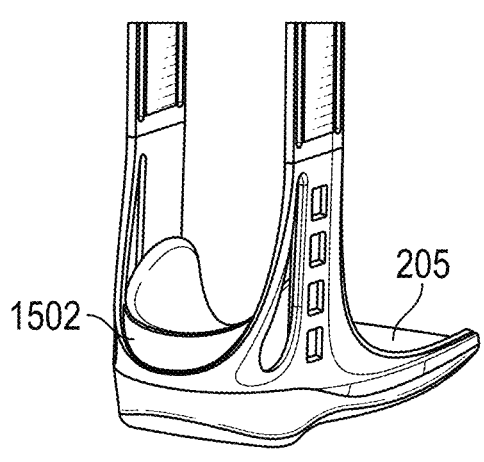

FIGS. 15A-15D illustrate several steps of a method of installing insole 205 into at least a pre-molded portion of brace 200, in accordance with some example embodiments. For example, FIG. 15A illustrates a side view, a perspective view from above and a perspective view from below insole 205. In some embodiments, insole 205 further includes a removable region 1502 where an Achilles tendon of the user is configured to rest, as illustrated in at least FIGS. 15A and 15D. As shown in FIG. 15B, insole 205 can be inserted and then secured or otherwise bonded to at least a portion of footbed 206, as shown in FIG. 15C. In addition, removable region 1502 of insole 205 can be cut away to accommodate bandaging and/or access the lower Achilles region of the foot of the user.

Discussion now turns to enhancement of heel strike/impact absorption of the brace 200. Typical wear patterns on used boots indicate that the initial heel strike occurs at the rear edges of the sole, as indicated by the sole damage shown in the dotted rectangular boxes 1602, 1604 in FIGS. 16A, and 16B. Accordingly, to reduce such heel strike impacts, under-boot sole 270 comprises an impact absorbing material. In some embodiments, a thicker, non-skid material is applied to regions of under-boot sole 270 corresponding to sole damage regions 1602, 1604 in FIGS. 16A and 16B.

Figure 17:
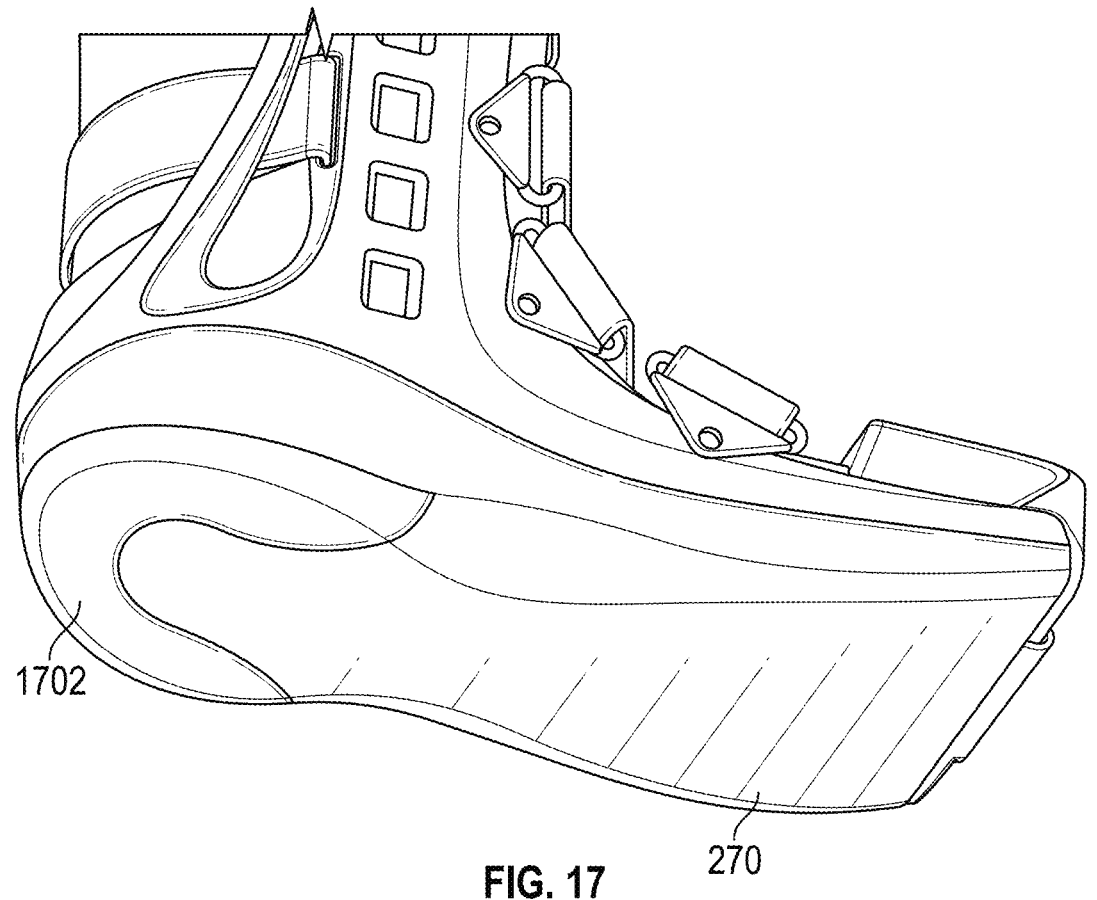
FIG. 17 illustrates a perspective view of an undersole with an enhanced impact region on the heel strike portion of the undersole, in accordance with some example embodiments.

For example, as illustrated in FIG. 17, under-boot sole 270 can comprise a heel strike region 1702 comprising a rubber-like material that is thicker than at least some other portions of under-boot sole 270 to absorb the heel strike to the floor as the user walks. In some embodiments, heel strike region 1702 can comprise an entire posterior portion of under-boot sole 270. In some other embodiments, heel strike region 1702 can comprise a portion that extends along a perimeter and a predetermined distance toward a center of such a posterior portion of under-boot sole 270, such that at least a central portion of the posterior portion of under-boot sole 270 is not included in the thicker, heel strike region 1702. In some embodiments, a surface of at least heel strike region 1702 can be textured and/or formed from a non-skid material.

Discussion now turns to liner 240, pump 290 and release valve 292 for adjusting an amount of pressure and/or support provided by liner 240 and at least one inflatable cavity disposed therein. As illustrated in the perspective view of liner 240 in FIG. 18A and the cross-sectional view of liner 240 in FIG. 18B, liner 240 can comprise air pump 290, pressure-release valve 292, and one or more air-tight, inflatable cavities (see FIGS. 19A and 20A) in fluid communication with air pump 290 and pressure-release valve 292 such that a desired, adjustable amount of pressure and/or support can be provided to one or more physical locations of the user's foot and/or lower leg associated with each of the one or more inflatable cavities.

Figure 18A:
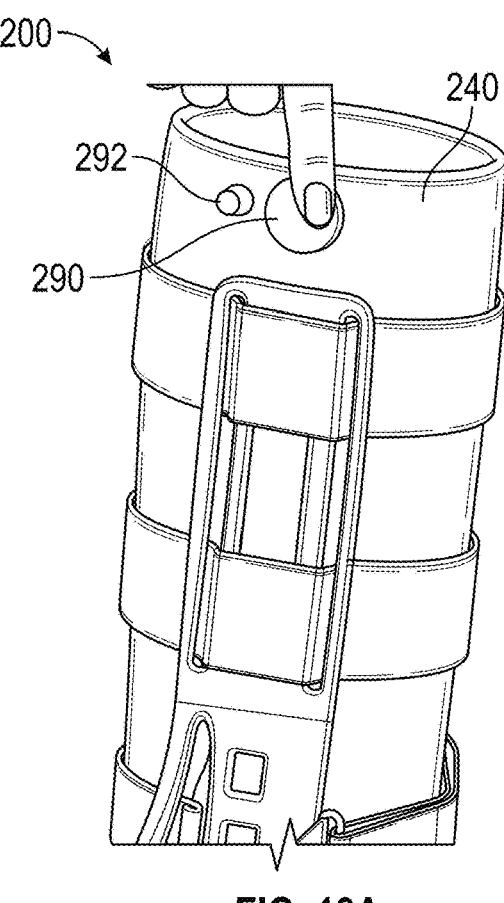
FIG. 18A illustrates a perspective view of a portion of a liner of a walking brace including a pump and release valve, in accordance with some example embodiments.
Figure 18B:
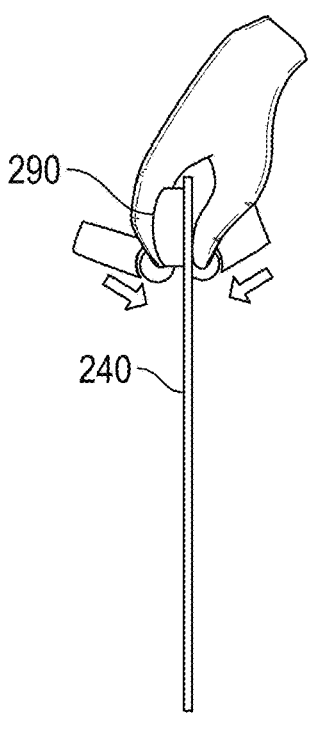
FIG. 18B illustrates a cross-sectional view of the liner of FIG. 18B, in accordance with some example embodiments.

As illustrated in FIGS. 18A and 18B, pump 290 and release valve 292 can be disposed within, and sufficiently close to an upper edge of, liner 240 such that the user can easily and comfortably adjust an amount of inflation of one or more inflatable cavities within liner 240 by pushing on the pump 290 and/or release valve 292 from the outside of the liner. Another advantage of positioning pump 290 and release valve 292 sufficiently close to the upper edge of liner 240 is that the user can alternatively pinch the pump bulb by simultaneously applying pressure from the outside and from the inside of liner 240. Such a pinch-actuation of pump 290 and/or of release valve 292 allows the use of hand strength to directly affect actuation, rather than relying on, typically, weaker arm strength when activation is affected at the length of a partially extended arm. By contrast, pumps and/or release valves disposed farther down a brace and/or liner than the inside length of a user's thumb, for example, would not allow for such alternative pinch-actuation of such a pump and/or release valve.

Figure 19A:
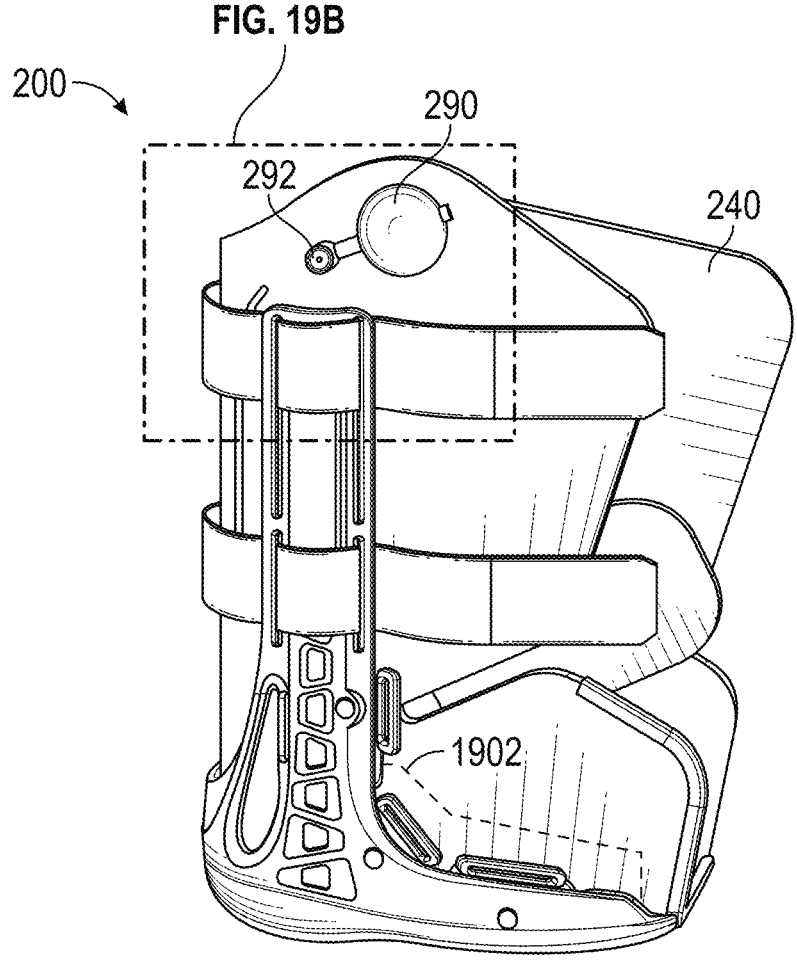
FIG. 19A illustrates a perspective view of a liner disposed within a walking brace, in accordance with some example embodiments.
Figure 19B:
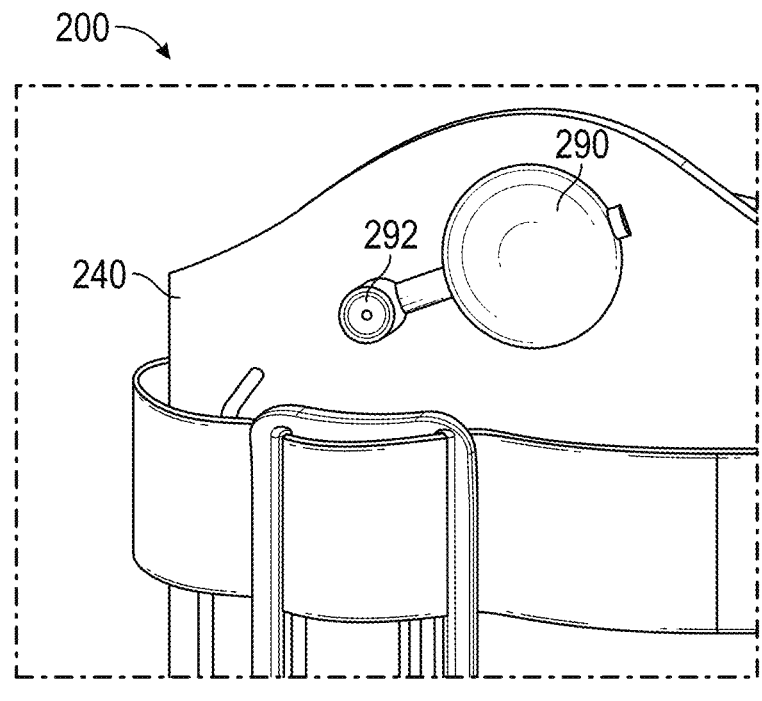
FIG. 19B illustrates a magnified view of the portion of the liner and walking brace in the dotted rectangular box of FIG. 19A.

FIG. 19A illustrates liner 240, as described above and further illustrating the least one inflatable cavity 1902, where liner 240 is disposed within brace 200. FIG. 19B provides a magnified view of the dotted rectangular box portion of FIG. 19A. As illustrated, pump 290 is in fluid communication with release valve 292. One or both of pump 290 and release valve 292 are also in fluid communication with inflatable cavity 1902, disposed within liner 240. In some embodiments, inflatable cavity 1902 may be disposed in portion of liner 240 configured to abut a portion of the user's foot. However, the present disclosure is not so limited and any number of inflatable cavities may be utilized and such inflatable cavities can be disposed within any suitable portion of liner 240.

Figure 20A:
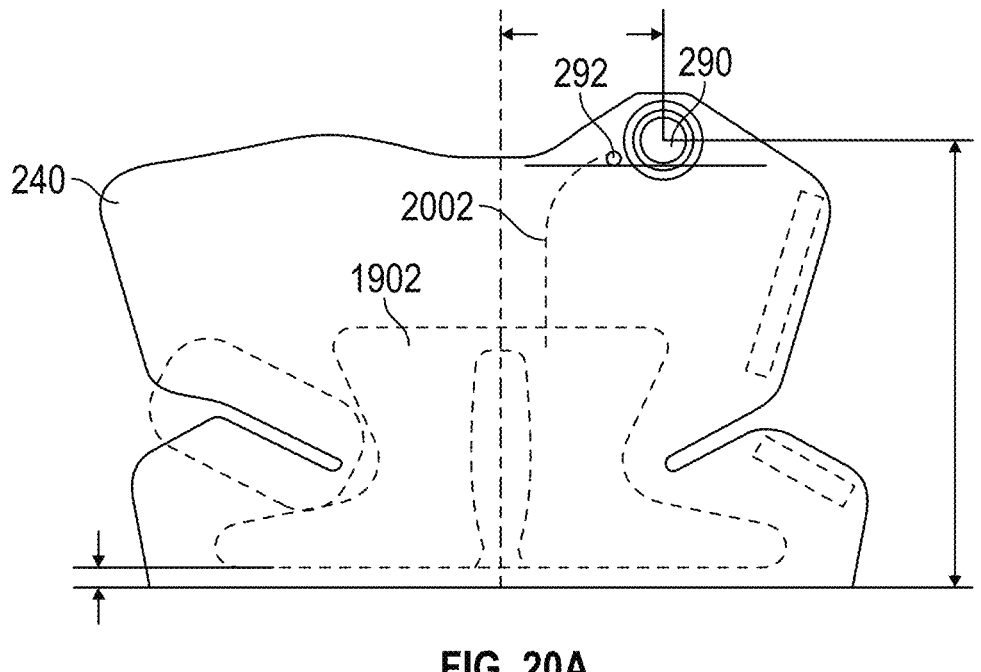
FIG. 20A illustrates a schematic view of a liner for a walking brace, in accordance with some example embodiments.
Figure 20B:
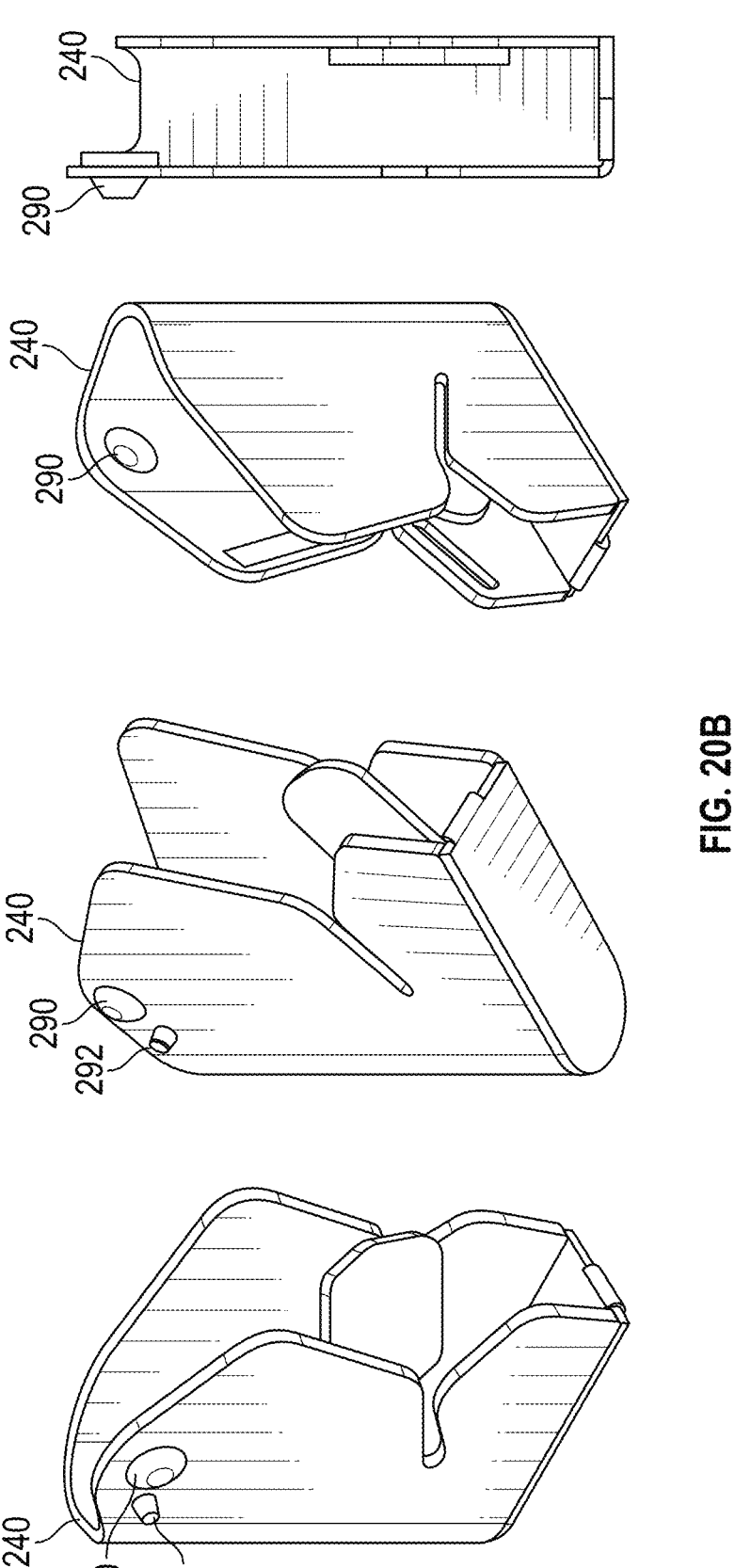
FIG. 20B illustrates several perspective and front schematic views of the liner of FIG. 20A.

FIG. 20A illustrates a flattened schematic view of liner 240 that shows an example orientation of pump 290, release valve 292 and at least one inflatable cavity 1902. FIG. 20B illustrates a front and several perspective schematic views of liner 240 as illustrated in FIG. 20A. As shown, pump 290 is in fluid communication with release valve 292 and release valve 292 is in fluid communication with inflatable cavity 1902 through a tube 2002. In FIG. 20A, inflatable cavity 1902 is illustrated as extending substantially along and within portions of liner 240 configured to abut medial and lateral sides of a foot of a user, as well as at least a portion of the user's ankle, but in some embodiments also a portion of the lower calf of the user. In some embodiments, inflatable cavity 1902 is disposed symmetrically within liner 240 such that a portion of inflatable cavity 1902 extending to one side of a vertical centerline of liner 240 is a substantial mirror image of a portion of inflatable cavity 1902 extending to the other side of the vertical centerline. However, the present disclosure is not so limited and inflatable cavity 1902 and/or any other inflatable cavity can be disposed in any other suitable portion of liner 240 and with any suitable orientation.

Discussion will now turn to a protective rim disposed around a perimeter of release valve 292 and configured to prevent accidental or inadvertent deflation of the one or more inflatable cavities 1902 of liner 240, in connection with at least FIGS. 21-23C.

Inadvertent deflation of inflatable cavities 1902 of liner 240 of walking brace 200 can cause discomfort and possible body fluid "puddling" around and below an injury. Inflatable cavities 1902 aid in providing comfort and mitigating such body fluid "puddling". Such inflatable cavities 1902 are inflated manually utilizing pump 290, which can be a bulb-like hand pump. Air and/or other fluid can be released from inflatable cavities 1902 utilizing release valve 292, which can comprise a push-button actuated valve. Such push buttons are easy to use and are less likely to leak or sustain damage from over rotating, as can more commonly happen when using a twisting, knob-type release valve. However, such push button type release valves can be prone to accidental activation.

The most popular method to prevent accidental pushing of a release button is to provide a protective cap that covers the button. While functional, such protective caps add cost and complexity to the release valves. Moreover, protective caps can be broken off or damaged. By contrast, a protective rim made a part of the release valve structure is static, does not move or flex, and is not easily damaged.

Figure 21:
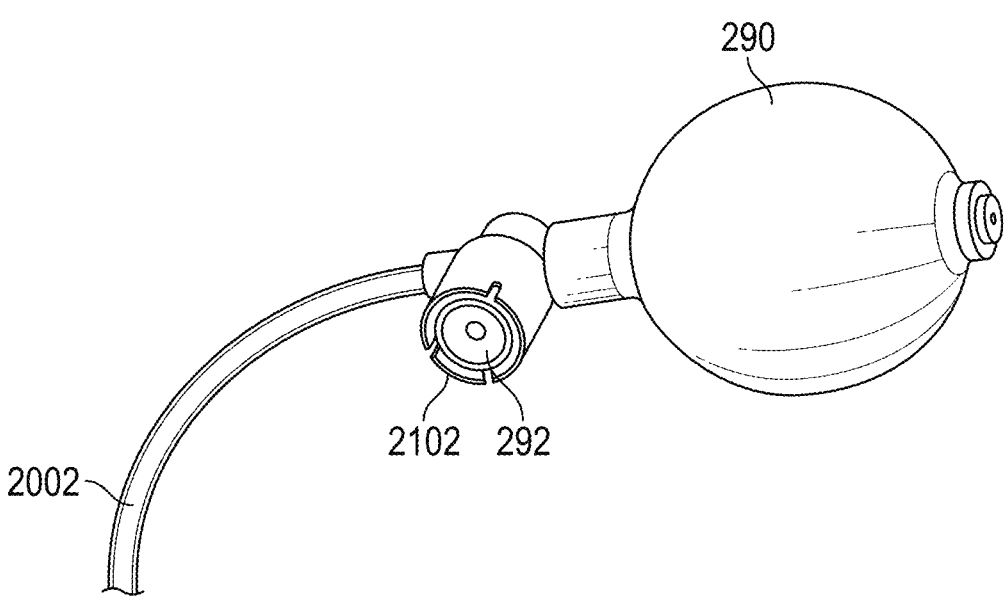
FIG. 21 illustrates a perspective view of a pump and release valve as disposed within a liner for a walking brace, in accordance with some example embodiments.
Figure 22:
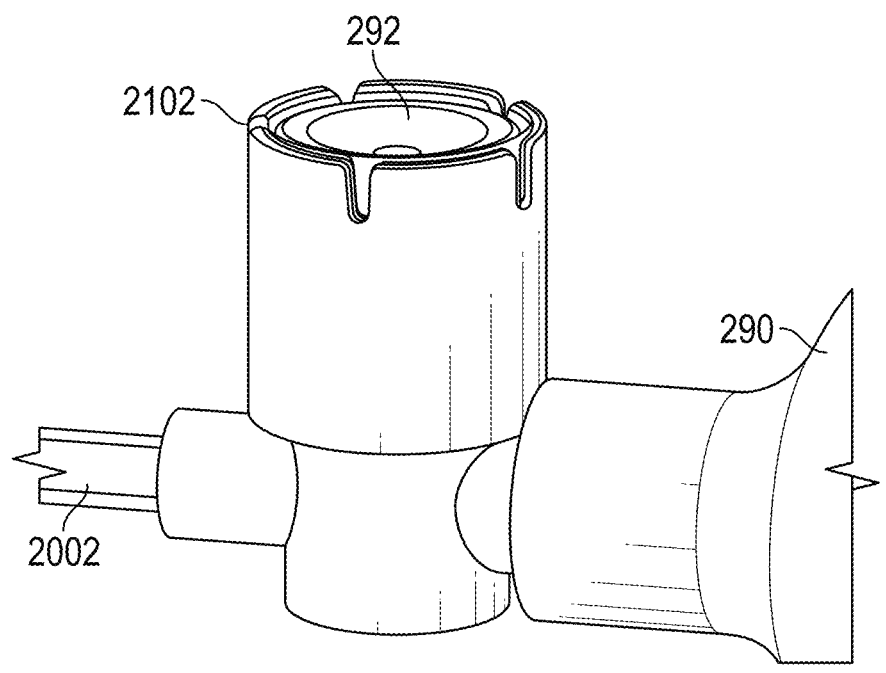
FIG. 22 illustrates a perspective view of the release valve of FIG. 21.
Figure 23A:
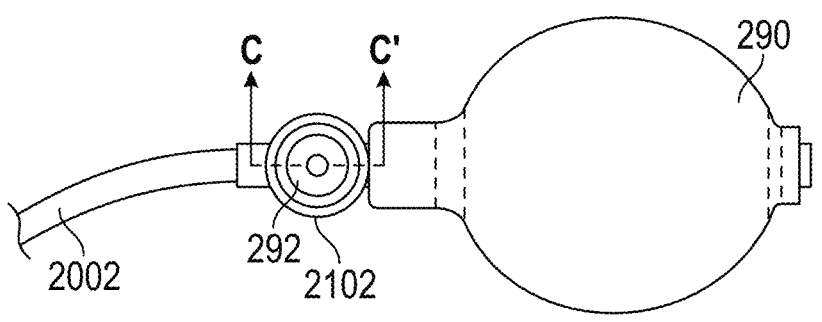
FIG. 23A illustrates a side schematic view of the release valve of FIG. 21.
Figure 23B:
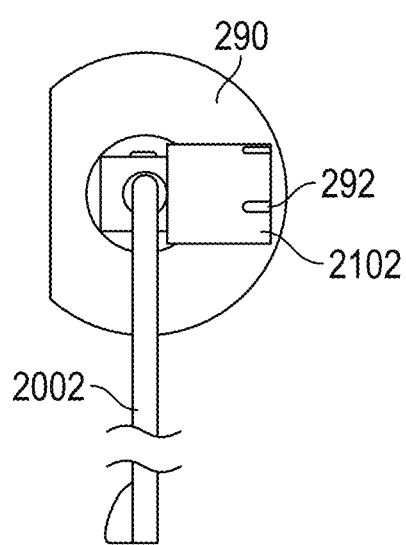
FIG. 23B illustrates another side schematic view of the release valve of FIG. 21 as viewed from the direction denoted "B" in FIG. 23A.
Figure 23C:
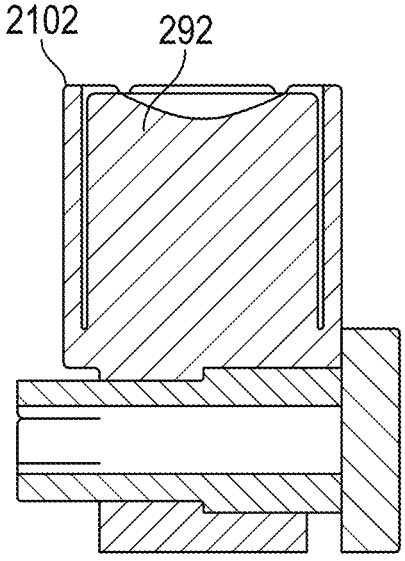
FIG. 23C illustrates a cross-sectional schematic view of the release valve of FIG. 21 as viewed along the cut line denoted C-C' in FIG. 23A.

Accordingly, to prevent accidental release of air or other fluid from Inflatable cavities 1902, release valve 292 can further include a crenulated type rim 2102, as illustrated in at least FIGS. 21 and 23C. FIG. 22 further illustrates a magnified view of rim 2102 and release valve 292, while FIGS. 23A-23C illustrate several side and cutaway views of pump 290, release valve 292 and/or rim 2102.

Rim 2102 can extend along substantially an entire perimeter of release valve 292 button and can also extend to a height slightly greater than a top or outside surface of the release valve 292 button, for example and not limitation 0.02 inches (0.5 millimeters) above the top or outside surface of release valve 292 button. Further, in some embodiments as illustrated in at least FIG. 23C, the release valve 292 button can have a substantially concave shape, providing tactile feedback as to the location of the center of the release valve 292 button.

Discussion will now turn to chafe and chafe lock features configured to allow a chafe to align with a direction of pull of one or more straps of a walking brace, such as brace 200.

Figure 24:
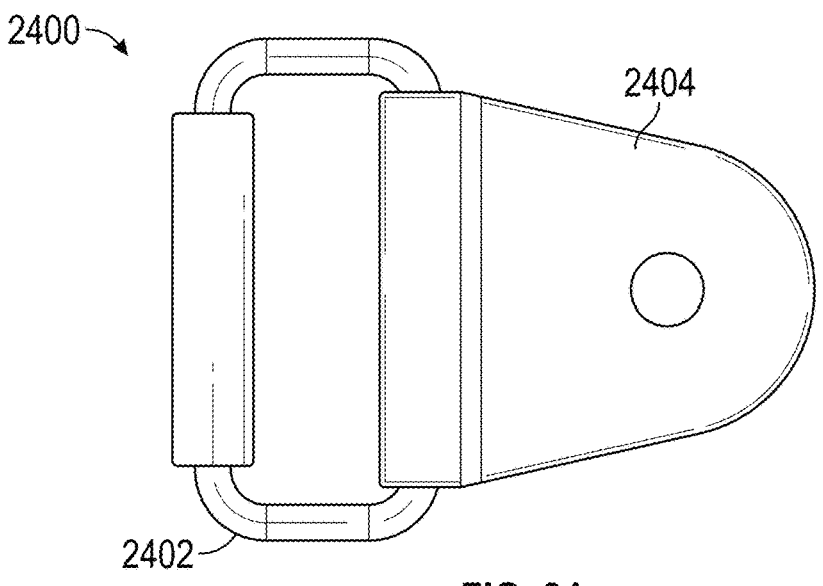
FIG. 24 illustrates a conventional chafe.

FIG. 24 illustrates a top view of a conventional chafe 2400. Chafe 2400 is an assembly comprising an attachment feature, also called a chape 2404, and a metal or plastic loop 2402 coupled thereto. Loop 2402 is configured to accommodate securing of a strap or a webbing. Chapes, or "caps" of various designs can be fitted to such a loop and are typically fabricated in the form of a plate, for example for utilization in a belt, as a belt buckle. However, conventional chafes 2400 are typically riveted to an item needing securing and are not configured to rotate, hinge, bend or otherwise flex and, so, are not configured to align with a direction of pull of one or more straps coupled to loop 2402. Accordingly, such conventional chafes 2400 cannot tightly bind, for example, a narrow leg into a walking brace, for example walking brace 200.

The present disclosure contemplates an alternative chafe assembly, comprising a chafe and a chafe lock that, together, allow the chafe to align with the direction of pull of a strap coupled to a loop of the chafe. Installation of such a chafe assembly requires no tools, is completely manual and, once the chafe is secured to its lock, the lock is configured to spin within its mounting aperture, which prevents a hinge region of the chafe from twisting while still allowing the chafe to bend and align with the direction of pull of a strap coupled to a loop of the chafe.

Figure 25:
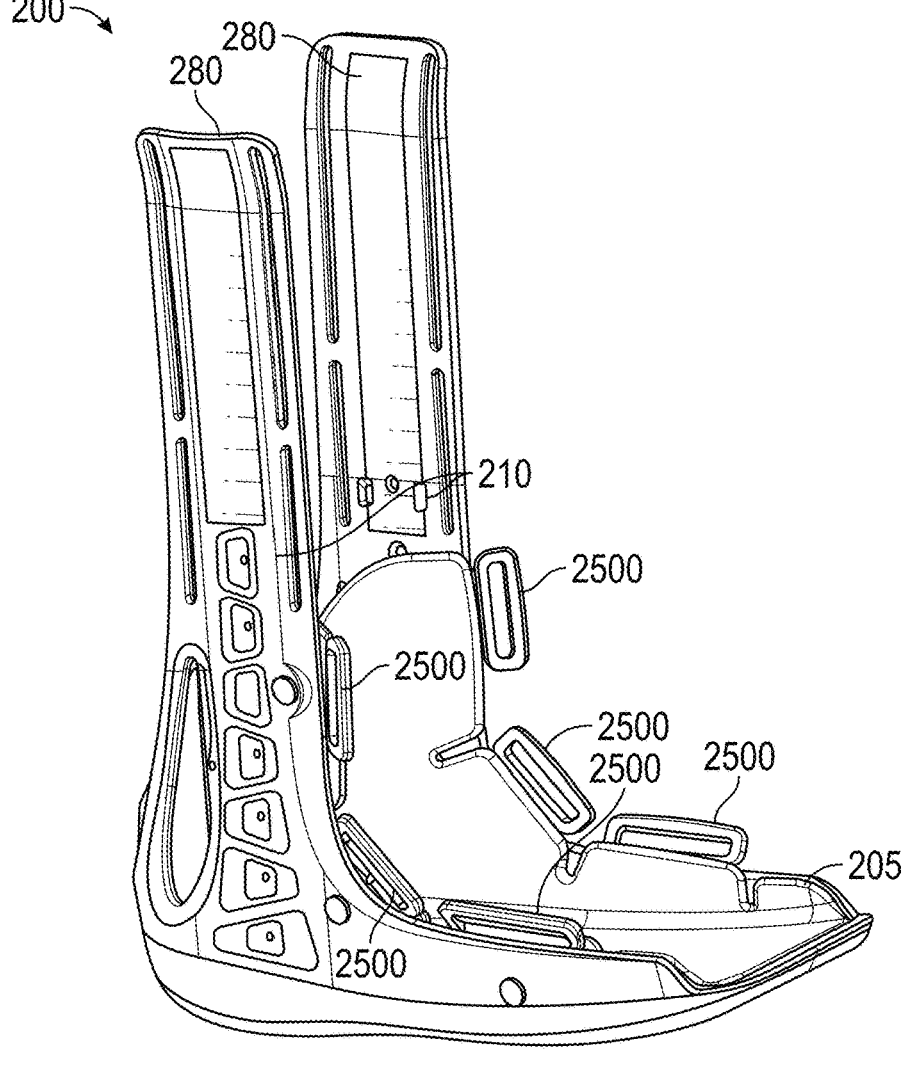
FIG. 25 illustrates a walking brace including a plurality of chafe assemblies, in accordance with some example embodiments.

FIG. 25 illustrates walking brace 200 having a plurality of rotatable chafe assemblies 2500 for securing one or more straps of brace 200, in accordance with some example embodiments. Chafe assembly 2500 comprises a chafe 2600, for example as described in more detail in connection with at least FIGS. 26A-26D, and a chafe lock 2700, for example as described in more detail in connection with at least FIGS. 27A-27E. Discussion now turns to chafe 2600 in connection with FIGS. 26A-26D.

Figures 26A, 26B, 26C, 26D:
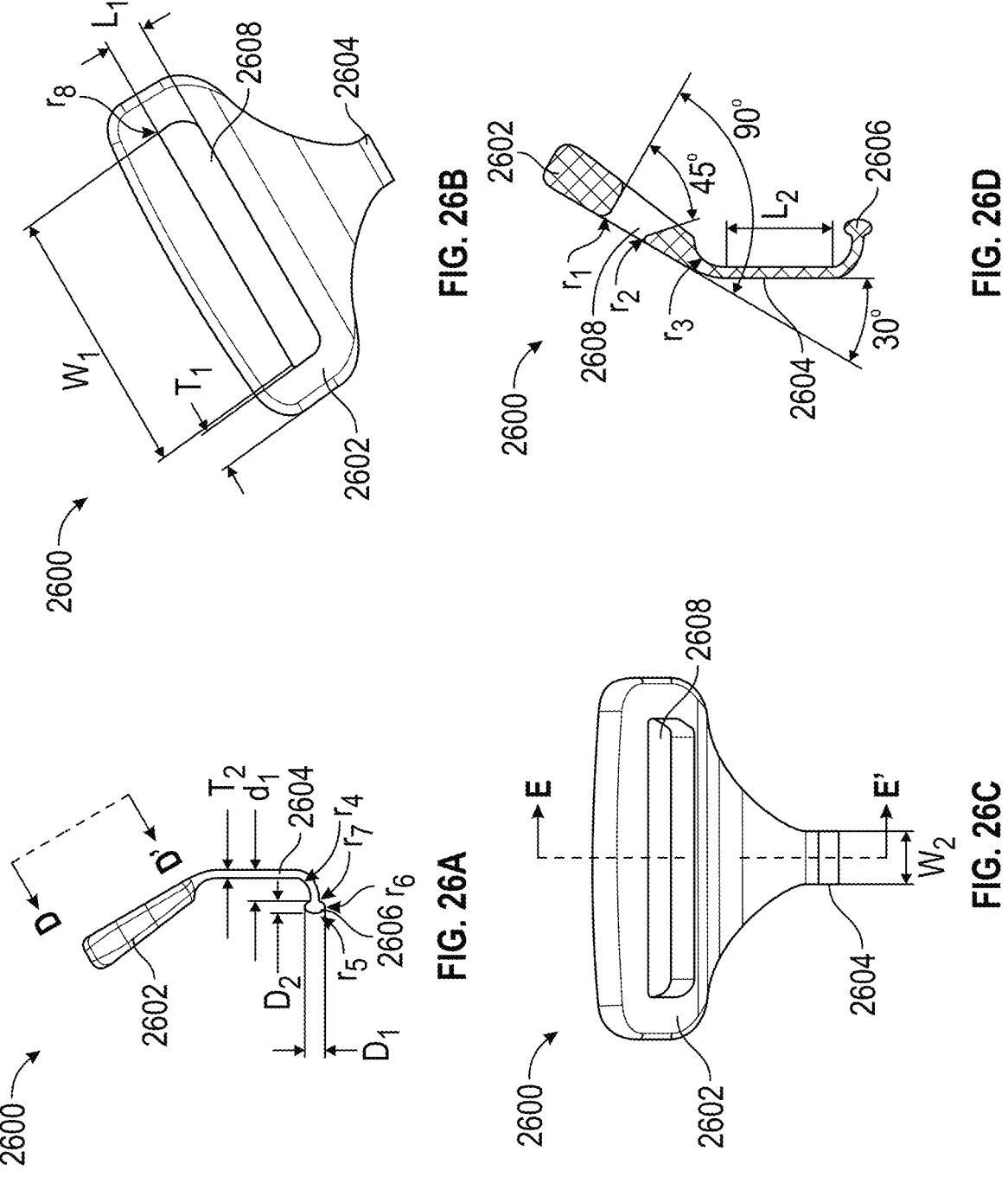
FIG. 26A illustrates a side view of a flexible, rotatable chafe, in accordance with some example embodiments.
FIG. 26B illustrates a top view of the chafe of FIG. 26A from the vantage point D-D' in FIG. 26A.
FIG. 26C illustrates a bottom view of the chafe of FIG. 26A from the opposite vantage point compared to FIG. 26B.
FIG. 26D illustrates a cross-sectional view of the chafe of FIG. 26A taken along the cut line E-E' in FIG. 26C.

FIG. 26A illustrates a side view of chafe 2600, in accordance with some example embodiments. FIG. 26B illustrates a top view of chafe 2600 viewed from the vantage point D-D' in FIG. 26A. FIG. 26C illustrates a bottom view of chafe 2600 viewed from the opposite vantage point as FIG. 26B. And FIG. 26D illustrates a cross-sectional view of chafe 2600 viewed along the cut-line E-E' in FIG. 26C. While several example dimensions will be described regarding certain aspects of chafe 2600, the present disclosure also contemplates chafe 2600 having any other suitable dimensions and/or construction.

Chafe 2600 comprises a head 2602, a neck 2604 and a locking end 2606. Head 2602 comprises a slot 2608 configured for receiving, for example, any of straps 222, 224, 226. In some embodiments, slot 2608 has a width $w_1$ of approximately 1.5 inches and a length $L_1$ of approximately 0.216 inches. However, as stated above, other widths are also contemplated, for example and not limitation, 2 inches. In some embodiments, a distal wall of slot 2608 is formed at a substantially 90° angle with respect to a top surface of head 2602 and may have a radius of curvature $r_1$ of approximately 0.06 inches therebetween. In some embodiments, the distal wall of slot 2608 may transition to the substantially perpendicular orientation of an adjacent sidewall along the $L_1$ lengthwise direction with a radius of curvature $r_8$ of approximately 0.02 inches. In some embodiments, a proximal wall of slot 2608 is formed at a substantially 45° angle with respect to a top surface of head 2602 and may have a radius of curvature $r_2$ therebetween of approximately 0.02 inches. Furthermore, in some embodiments, a sidewall of head 2602 may have a thickness of 0.23 inches, as measured along the width-wise ($w_1$) direction between slot 2608 and a lateral outside edge of head 2602.

In some embodiments, head 2602 may transition to neck 2604 by narrowing to a width $w_2$ of, for example, 0.3 inches, and a thickness $T_2$ of, for example, 0.04 to 0.05 inches. In some embodiments, the first transition from head 2602 to neck 2604 may follow a radius of curvature $r_3$ of, for example, 0.1 inches, as measured at a backside of the transition, and neck 2604 may extend away from head 2602 at an angle of, for example, 30° relative to the top surface of head 2602. In some embodiments, neck 2604 may extend from the first transition for a length $L_2$ of approximately 0.451 inches and then transition, again, bending, for example, approximately another 90° from neck 2604 to locking end 2606 along a radius of curvature $r_4$ of, for example, 0.1 inches, as measured at a backside of the second transition. The relative thinness of neck 2604, especially at and adjacent to the portion at radius of curvature $r_4$, allows sufficient flexing and/or bending of neck 2604 such that chafe 2600 extends substantially in the direction of tension imposed by a strap coupled within slot 2608, thereby allowing a more secure fit of walking brace 200.

In some embodiments, locking end 2606 comprises a substantially cylindrical feature having a substantially ovoid or elliptical cross-section. In some such embodiments, the substantially cylindrical feature of locking end 2606 may have a major diameter $D_1$ of, for example, 0.11±0.003 inches, a minor diameter $D_2$ of, for example, 0.063±0.003 inches and may be offset from a backside surface of neck 2604 by a distance $d_1$ of, for example, 0.135 inches. Accordingly, the substantially cylindrical feature may have various radii of curvature along the different portions of its surface. For example, a radius of curvature $r_5$ along a portion extending along the major diameter $D_1$ may be, for example, 0.065 inches, a radius of curvature $r_6$ along a portion extending along the minor diameter $D_2$ may be, for example, 0.025 inches, and a radius of curvature $r_7$ at a transition between the substantially cylindrical feature and neck 2604 may be, for example, 0.01 inches. This substantially cylindrical feature is configured to slide into a slot of chafe lock 2700 as will be described in more detail in connection with FIGS. 27A-27E.

Figure 27A:
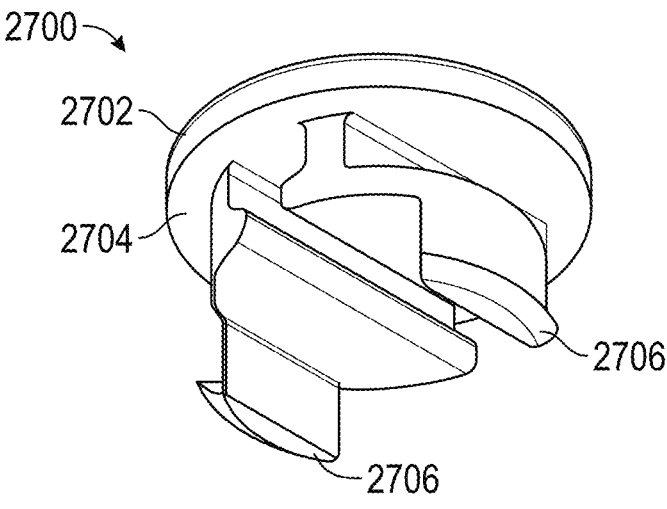
FIG. 27A illustrates a perspective view of a chafe lock, in accordance with some example embodiments.
Figure 27B:
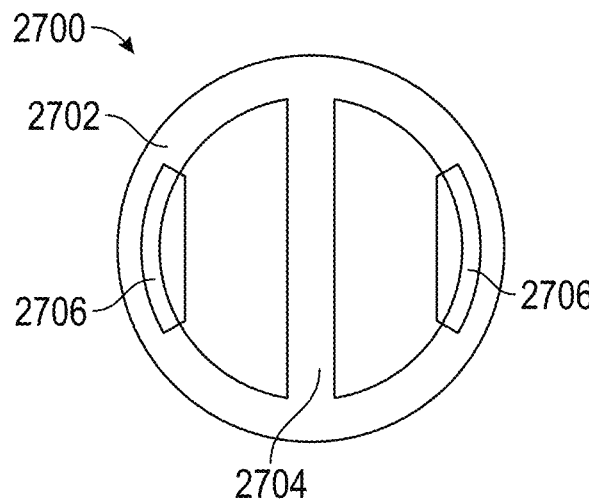
FIG. 27B illustrates a bottom view of the chafe lock of FIG. 27A.
Figure 27C:
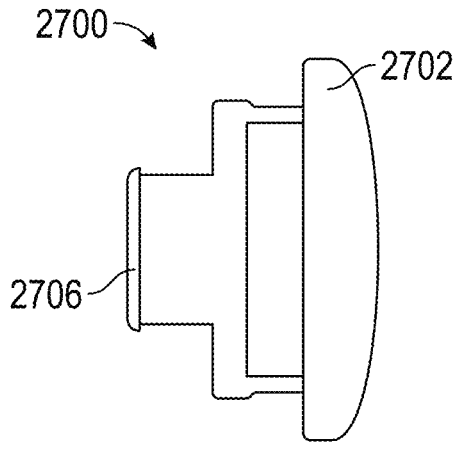
FIG. 27C illustrates a side view of the chafe lock of FIG. 27A.
Figure 27D:
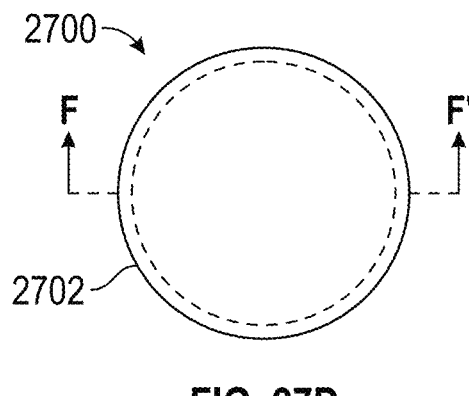
FIG. 27D illustrates a top view of the chafe lock of FIG. 27A.
Figure 27E:
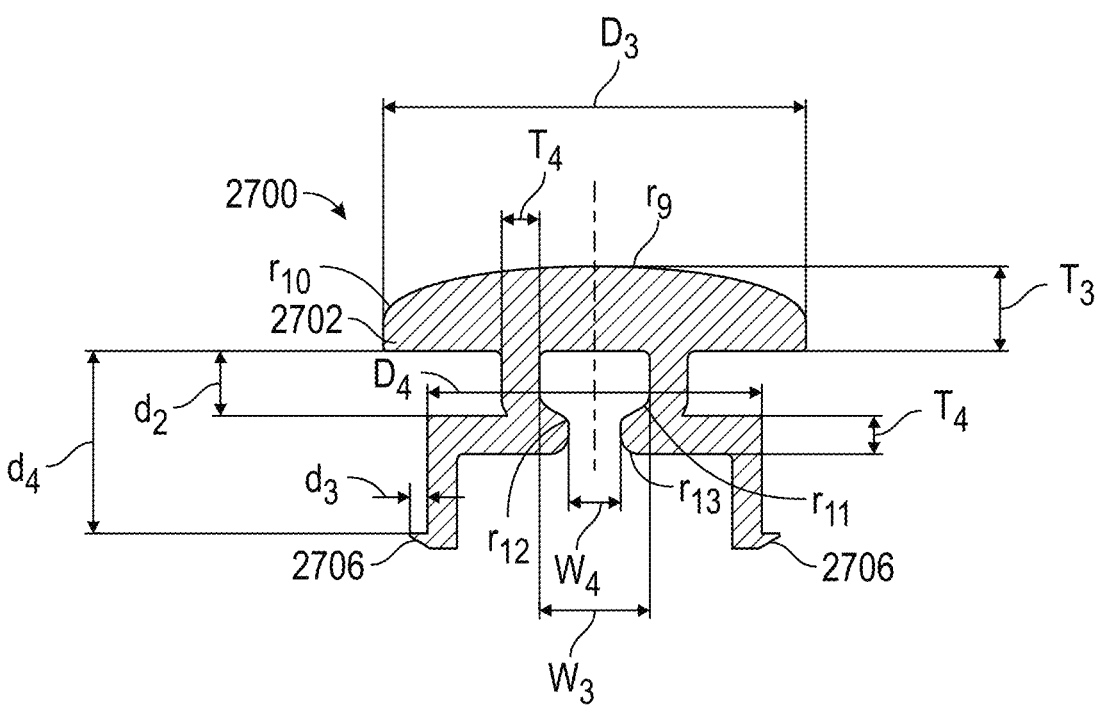
FIG. 27E illustrates a cross-sectional view of the chafe lock of FIG. 27A, taken along the cutline F-F' in FIG. 27D.

FIG. 27A illustrates a perspective view of chafe lock 2700, in accordance with some example embodiments. FIG. 27B illustrates a bottom view of chafe lock 2700. FIG. 27C illustrates a side view of chafe lock 2700. FIG. 27D illustrates a top view of chafe lock 2700. And FIG. 27E illustrates a cross-sectional view of chafe lock 2700 viewed along the cut-line F-F' in FIG. 27D.

Chafe lock 2700 comprises a cap 2702, a slot 2704 disposed underneath cap 2702 and a plurality of snap clips 2706 disposed underneath cap 2702 and slot 2704. Slot 2604 is configured to receive locking end 2606 of chafe 2600, specifically the substantially cylindrical feature having the substantially ovoid or elliptical cross-section described above, by sliding laterally over locking end 2606 such that the substantially cylindrical feature is secured within slot 2604. An underside of cap 2702 is configured to abut a first side of an aperture within walking brace 200, while the plurality of snap clips 2706 are configured to extend through and snap around a second side of the aperture, thereby securing chafe lock 2700 within the aperture while also allowing chafe lock 2700, and attached chafe 2600, to rotate freely within the aperture. In some embodiments, the aperture, chafe lock 2700 and/or chafe 2600 may be configured such that chafe lock 2700 and attached chafe 2600 are configured to rotate freely within a predetermined, desired range of rotation within the aperture and prevented from rotating beyond or outside that predetermined, desired range of rotation. In some embodiments, such a desired range of rotation would allow chafe 2600 to always point substantially in a desired direction and/or orientation with respect to the aperture, increasing user convenience. While several example dimensions will be described regarding certain aspects of chafe lock 2700, the present disclosure also contemplates chafe lock 2700 having any other suitable dimensions and/or construction.

Cap 2702 can have a substantially circular shape and may have a diameter $D_3$ of, for example, 0.445 inches, and a thickness $T_3$ of, for example, approximately 0.09 inches. In some embodiments, cap 2702 has a convex upper surface having a major radius of curvature $r_9$ of, for example, 0.639 inches and a minor radius of curvature $r_{10}$ of, for example, 0.03 inches at its edges.

In some embodiments, slot 2704 has an internal depth $d_2$ of, for example, 0.068±0.003 inches, an internal width $w_3$ of, for example, 0.115±0.003 inches, and an opening width $w_4$ of, for example 0.05±0.003 inches. Opening width $w_4$ being narrower than internal width $w_3$ allows slot 2704 to receive and retain locking end 2606 of chafe 2600. In some embodiments, the opening of slot 2704 may have a radius of curvature $r_{12}$ at its top edge of, for example, 0.008 inches and a radius of curvature $r_{13}$ at its bottom edge of, for example, 0.002 inches. In some embodiments, sidewalls of slot 2704 may have a thickness $T_4$ of, for example, 0.04 inches and a radius of curvature $r_{11}$ therebetween of, for example, 0.028 inches.

In some embodiments, the plurality of snap clips 2706 may have a substantially circular or cylindrical shape, substantially centered about a centerline of cap 2702. In some embodiments, snap clips 2706 may have an outer circular diameter $D_4$ of, for example, 0.353±0.003 inches, and may further comprise protrusions with a beveled lower edge that extends outward from the outer circular diameter by a distance $d_3$ of, for example, 0.02±0.003 inches. A distance $d_4$ between an underside of cap 2702 and a top side of these protrusions may be slightly larger than a depth or thickness of the aperture in brace 200 in which chafe lock 2700 is configured to be secured, for example, 0.19±0.005 inches. Accordingly, snap clips 2706 may have a thickness suitable to allow them to deflect slightly when pushed into the aperture of brace 200 but to snap back to their original shape and orientation once the protrusions clear the backside of the aperture, thereby rotatably securing chafe lock 2700 in the aperture.

Figure 28A:
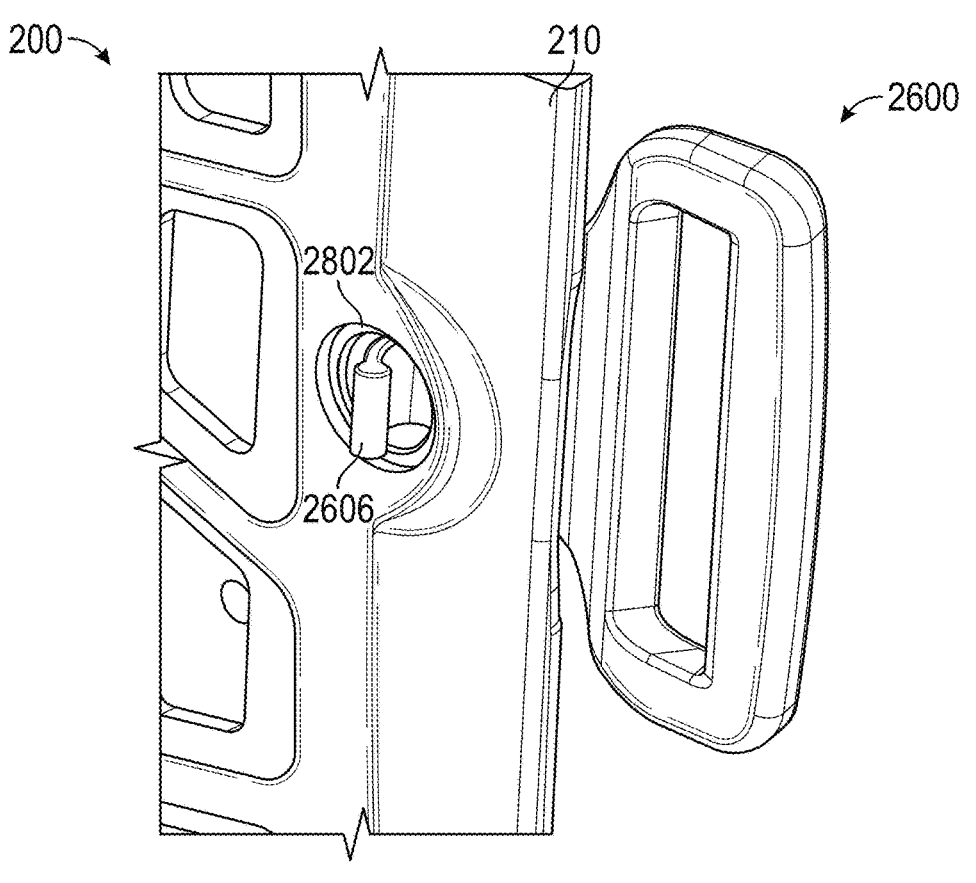
FIG. 28A illustrates installation of a chafe into an aperture of a walking brace, in accordance with some example embodiments.
Figure 28B:
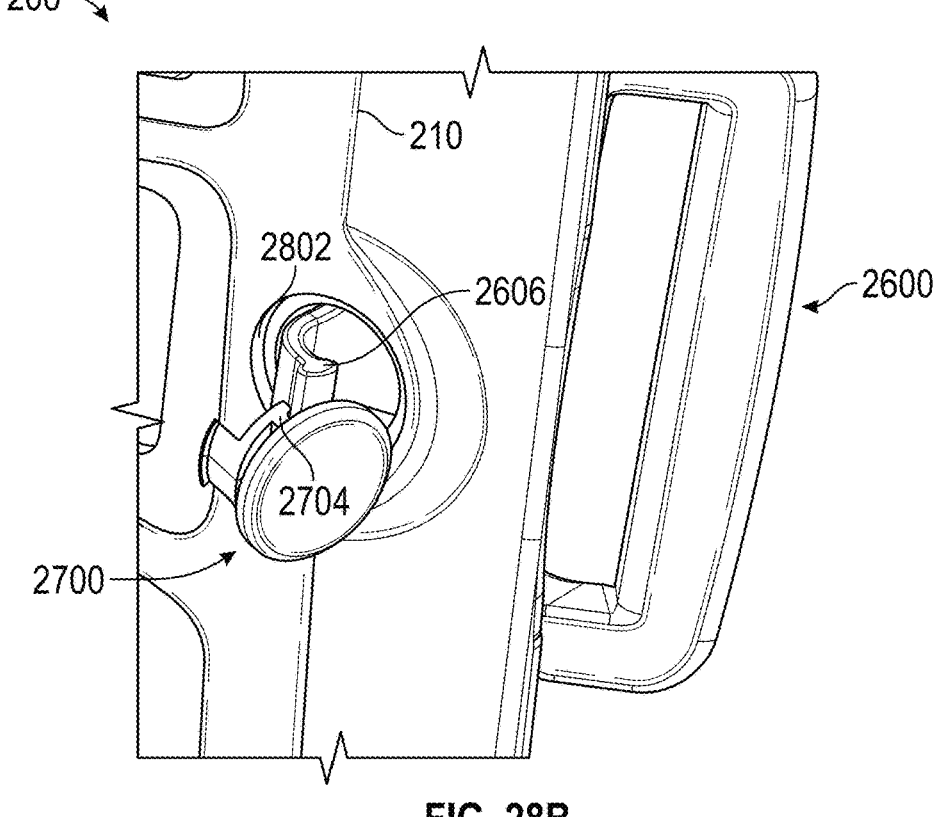
FIG. 28B illustrates installation of a chafe lock onto a locking end of the chafe of FIG. 28A, in accordance with some example embodiments.
Figure 28C:
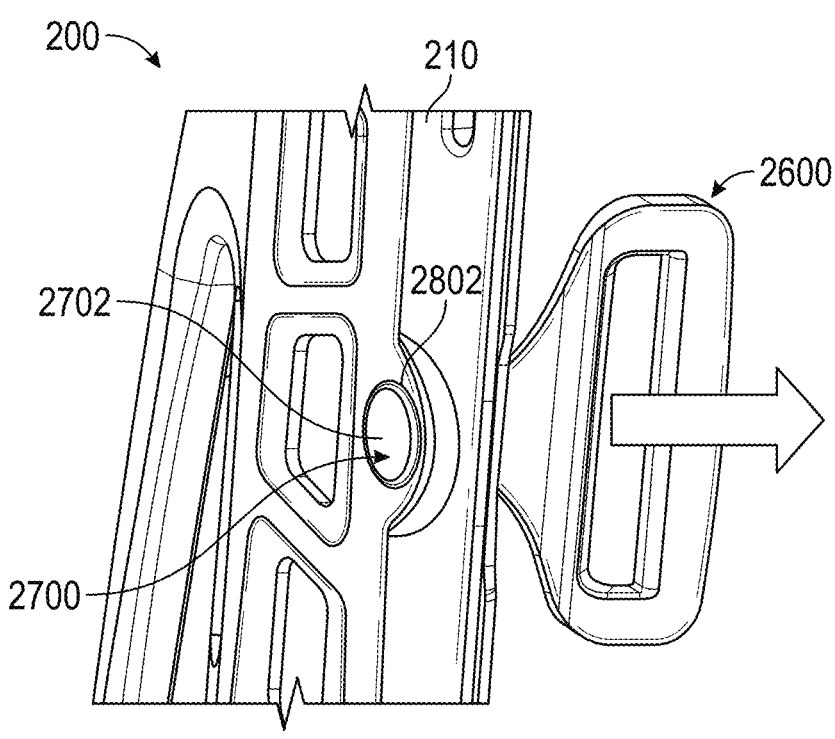
FIG. 28C illustrates securing of the chafe lock and locking end of the chafe of FIGS. 28A and 28B into the aperture of the walking brace, in accordance with some example embodiments.
Figure 28D:
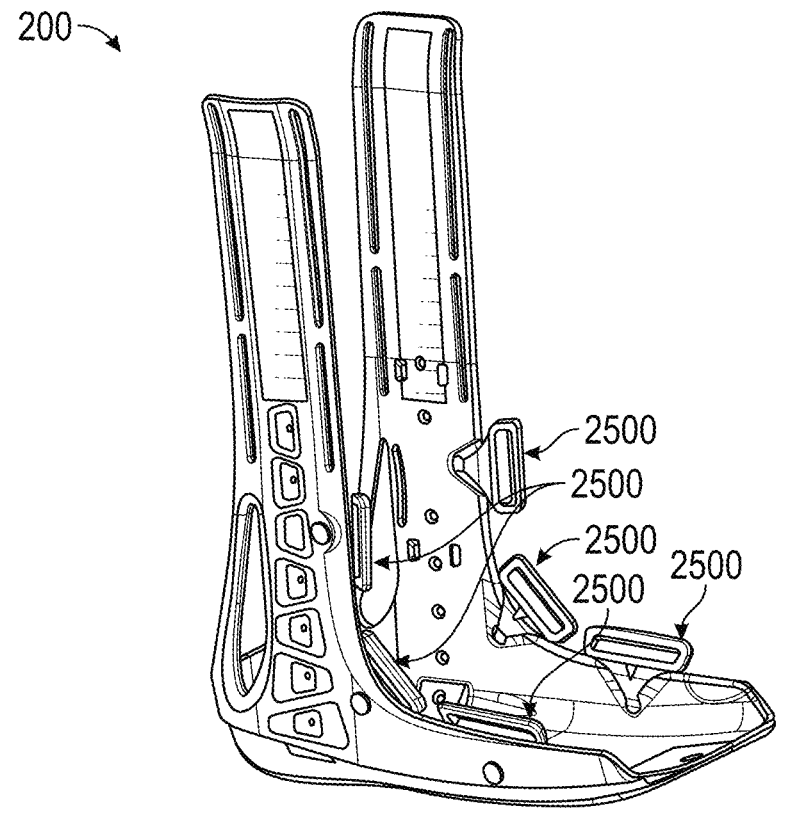
FIG. 28D illustrates the walking brace having a plurality of chafe assemblies, each comprising the chafe and chafe lock as described in FIGS. 28A-28C.

An example method of securing the chafe 2600 and chafe lock 2700 in an aperture of walking brace 200 will now be described in connection with FIGS. 28A-28D. As illustrated in FIG. 28A, locking end 2606 of chafe 2600 is pushed through aperture 2802 of walking brace 200. In some embodiments, aperture(s) 2802 of walking brace 200 may be disposed in uprights 210. As illustrated in FIG. 28B, chafe lock 2700 is slid onto the portion of locking end 2606 of chafe 2600 protruding through aperture 2802. Specifically, the substantially cylindrical feature of locking end 2606 is slid laterally into slot 2704 of chafe lock 2700. As illustrated in FIG. 28C, chafe 2600 is pulled back away from aperture 2802 such that chafe lock 2700 is pulled into and rotatably secured within aperture 2802. Specifically, by pulling head 2602 of chafe 2600 away from aperture 2802, an underside of cap 2702 of chafe lock 2700 is brought into direct contact with at least a proximal portion of aperture 2802 and the protrusions of the plurality of snap clips 2706 snap into place around a backside of aperture 2802, thereby rotatably securing chafe lock 2700 within aperture 2802. FIG. 28D illustrates a plurality of chafe assemblies, each including a chafe 2600 and chafe lock 2700 rotatably secured in a respective aperture of walking brace 200, substantially as described above.

Figure 29A:
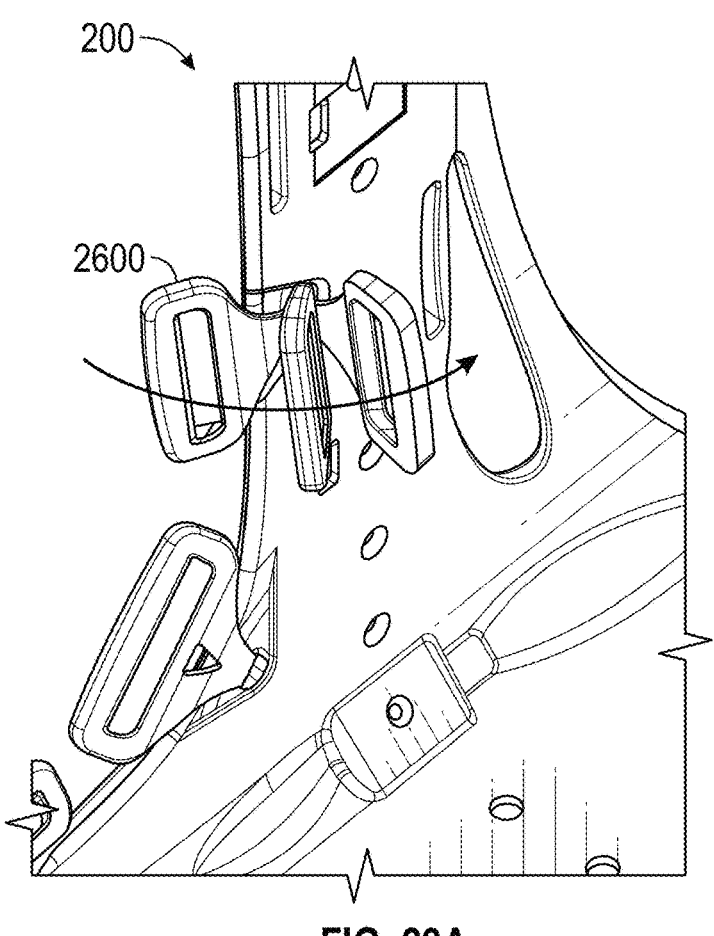
FIGS. 29A and 29B illustrate a flexibility feature of the chafe of FIGS. 26A-26D, in accordance with some example embodiments.
Figure 29B:
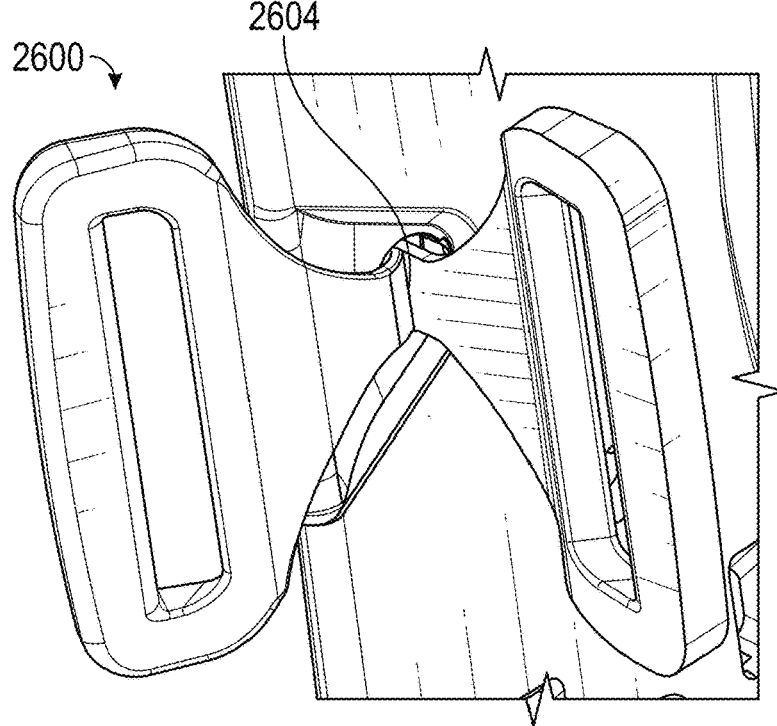

As illustrated in FIGS. 29A and 29B, chafe 2600 is configured to flex or bend to varying degrees and extend substantially in a direction of a tension exerted on chafe 2600 by a strap coupled to head 2602. This flexibility is provided, at least in part, by the relative narrowness of neck 2604 of chafe 2600 as described above.

Figure 30A:
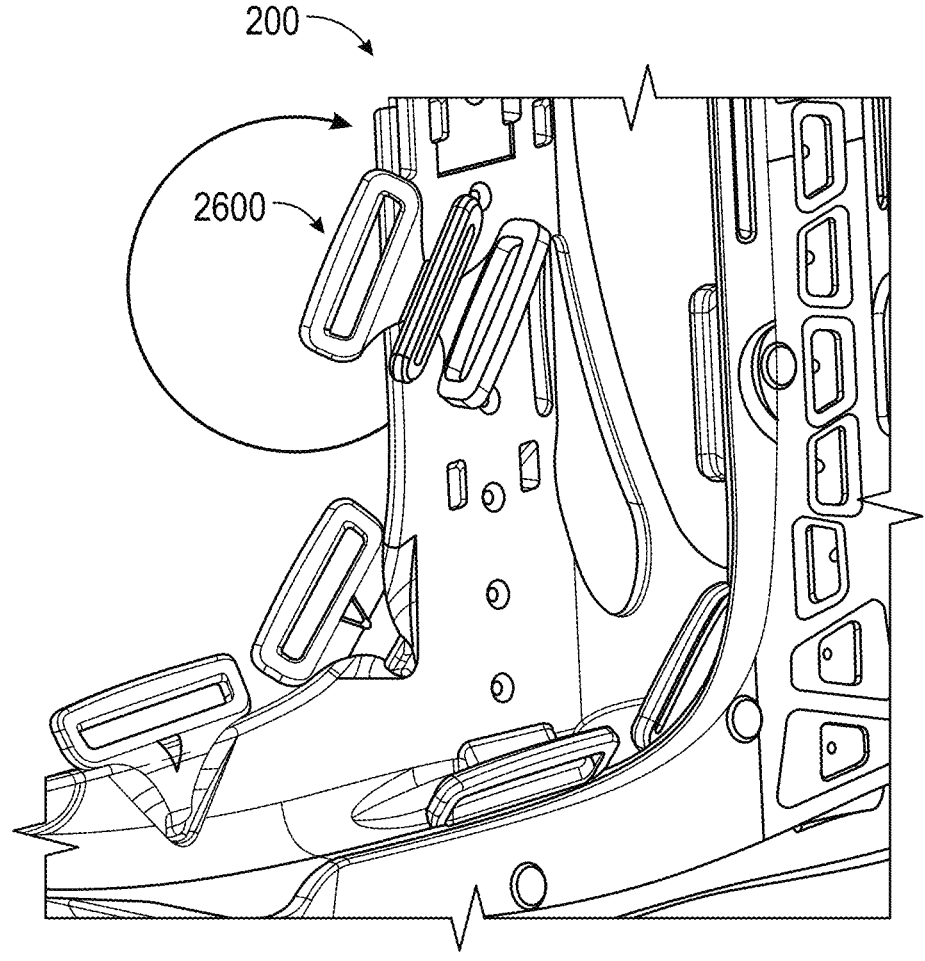
FIGS. 30A-30C illustrate a rotatability feature of the chafe and chafe lock of FIGS. 26A-27E, in accordance with some example embodiments.
Figure 30B:
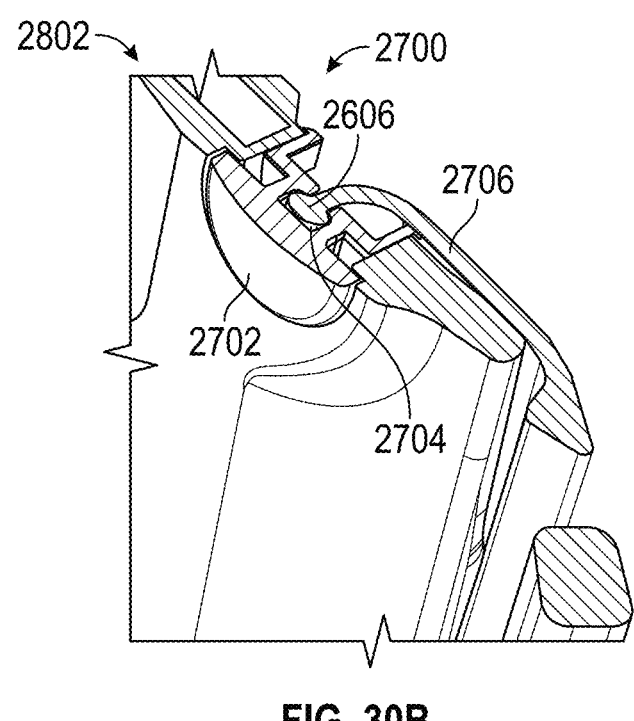
Figure 30C:
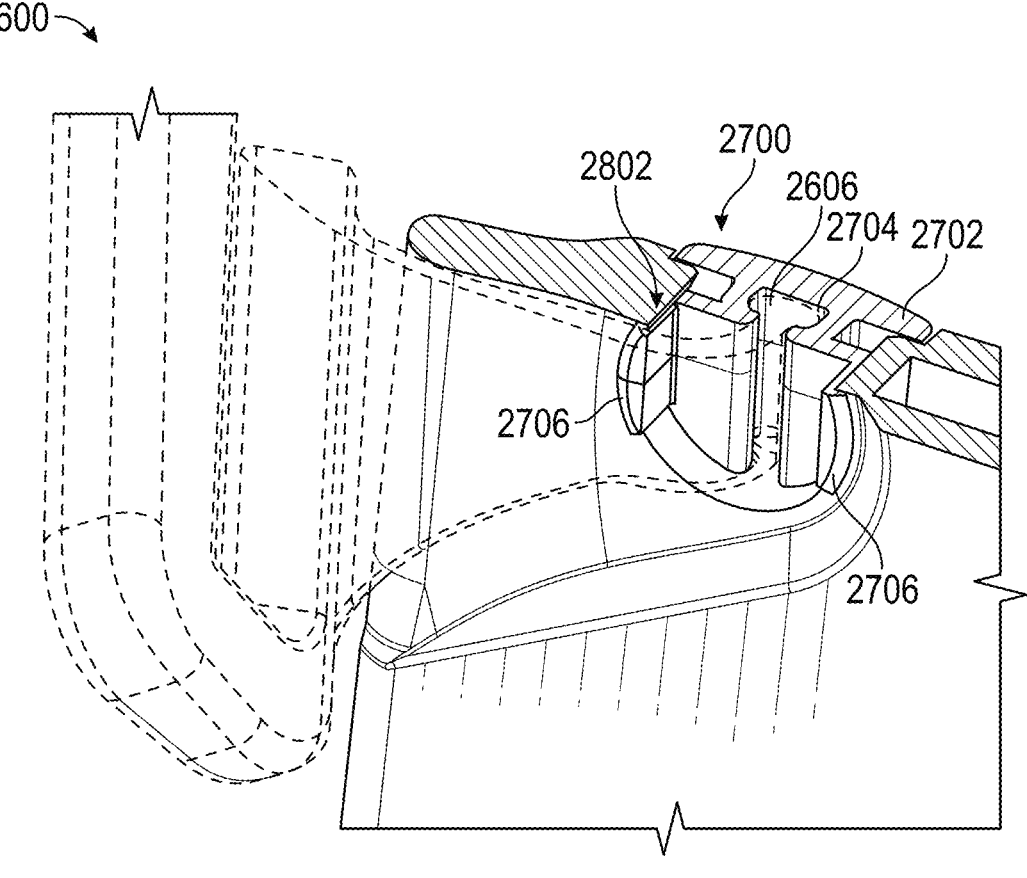

Moreover, as illustrated in FIGS. 30A-30C, chafe 2600 and chafe lock 2700 are further configured to rotate while secured within aperture 2802 by virtue, at least, of locking end 2606 of chafe 2600 being secured within slot 2704 of chafe lock 2700 and chafe lock 2700 being rotatably secured within aperture 2802. Specifically, an underside of cap 2702 of chafe lock 2700 is in direct physical contact with a proximal edge of aperture 2802 and the protrusions of snap clips 2706 are snapped into place around a backside of aperture 2802. Moreover, locking end 2606 of chafe 2600 is prevented from sliding out of slot 2704 of chafe lock 2700 at least by the sidewalls of aperture 2802 blocking slot 2704.

Modifications to the aforementioned embodiments are likewise contemplated. The walking brace may be secured to the limb of a wearer using one of three alternative configurations. Any combination of features described anywhere in this disclosure are also contemplated.

Figure 31A:
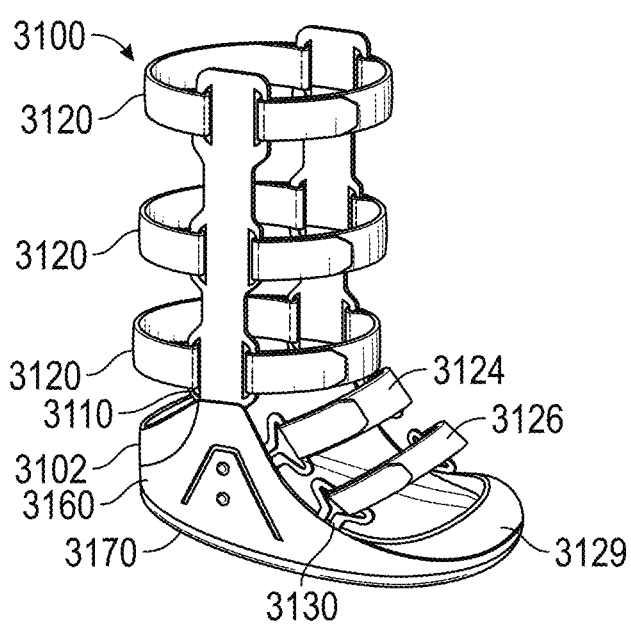
FIG. 31A illustrates a perspective view of an alternative walking brace, in accordance with some example embodiments.
Figure 31B:
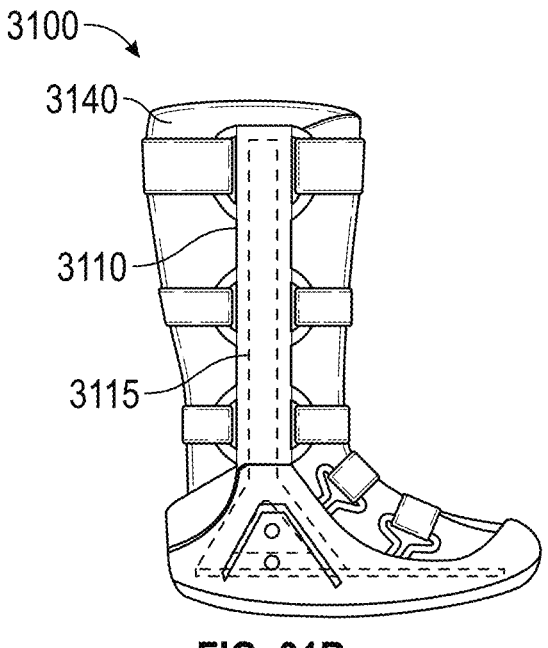
FIG. 31B illustrates a side view of the alternative walking brace of FIG. 31A, in accordance with some example embodiments.
Figure 31C:
FIG. 31C illustrates a footbed profile of the alternative walking brace of FIGS. 31A and 31B, in accordance with some example embodiments.

FIGS. 31A-31C illustrate a first additional and/or alternative configuration for a walking brace, in accordance with some example embodiments. For example, FIG. 31A illustrates a perspective view of a walking brace 3100, in accordance with some example embodiments. FIG. 31B illustrates a side view of brace 3100 of FIG. 31A, in accordance with some example embodiments. And FIG. 31C illustrates a top view of a footbed profile of brace 3100 of FIG. 31A, in accordance with some example embodiments.

Walking brace 3100 comprises a continuous plastic, EVA or other suitable material that forms a footbed 3160, outer sole 3170 and an upright 3110 on either side of brace 3100 overmolded onto a semi-rigid metallic or plastic stay 3115. In some embodiments, outer sole 3170 is non-slip, comprising a tread pattern formed in the EVA foam. Alternatively, a non-slip tread can be adhered to outer sole 3170. Such a one-piece, continuous plastic overmold eliminates the need for typical riveting of formable aluminum upright bars to a rigid plastic boot foot-bed. Integration of metallic stay(s) 3115 with footbed 3160 and uprights 3110 allows walking forces on boot 3100 to be shared by the plastic of uprights 3110 and metallic stay(s) 3115. In some embodiments, metallic stay(s)/bar(s) 2115 can comprise annealed aluminum. However, the present disclosure is not so limited and any suitable metallic and/or semi-rigid plastic material is also contemplated. As illustrated in FIGS. 31A and 31B, the overmold material also forms an integral toe cover 229 and an integral heel cover 3102, one or both of which can provide "bump" protection. In some embodiments, toe cover 3129 and heel cover 3102 can be removed by cutting, unattaching and/or otherwise tearing one or both off.

Walking brace 3100 comprises at least one upright strap 3120, configured to secure a lower leg of a user into brace 3100. Upright strap(s) 3120 can couple to and/or be threaded through at least a portion of upright 3110. In some embodiments, two or more upright straps 3120 can be coupled and/or threaded through at least a portion of upright extension 3110. As illustrated in FIG. 31A, walking brace 3100 does not include any hook/loop strips or fasteners on an inside surface of uprights 3110.

Brace 3100 further includes a plurality of lower straps, for example, including a proximal foot strap 3124 configured to wrap at least partly around and/or against a proximal portion of the foot of the user. In some embodiments, the plurality of lower straps includes a distal foot strap 3126 configured to wrap at least partly around and/or against a portion of the foot of the user distal to the proximal portion discussed above.

In some embodiments, one or more of straps 3124, 3126 are configured to couple to a respective one of a plurality of chafes 3130, which are each configured to rotatably and/or flexibly secure one side of the respective strap to brace 3100. Chafes 3130 can be as described in connection with any chafe in this disclosure. Alternatively, chafes 3130 can comprise D-rings molded into brace 3100, while still retaining sufficient flexibility to bend in a direction of tension exerted by one or more straps coupled thereto.

Brace 3100 may further comprise a liner 3140 comprising a soft, absorbent and, in some case, breathable, material configured to support and/or pad a foot and lower leg of a user. Liner 3140 can comprise any liner as previously described anywhere in this disclosure.

Figure 32A:
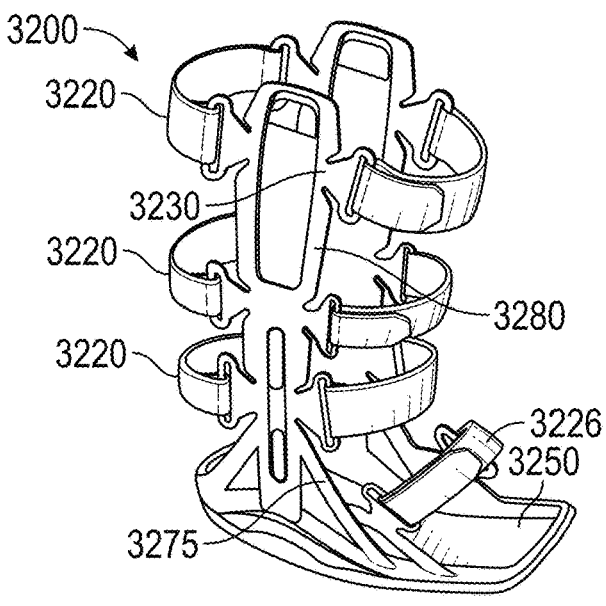
FIG. 32A illustrates a perspective view of another alternative walking brace, in accordance with some example embodiments.
Figure 32B:
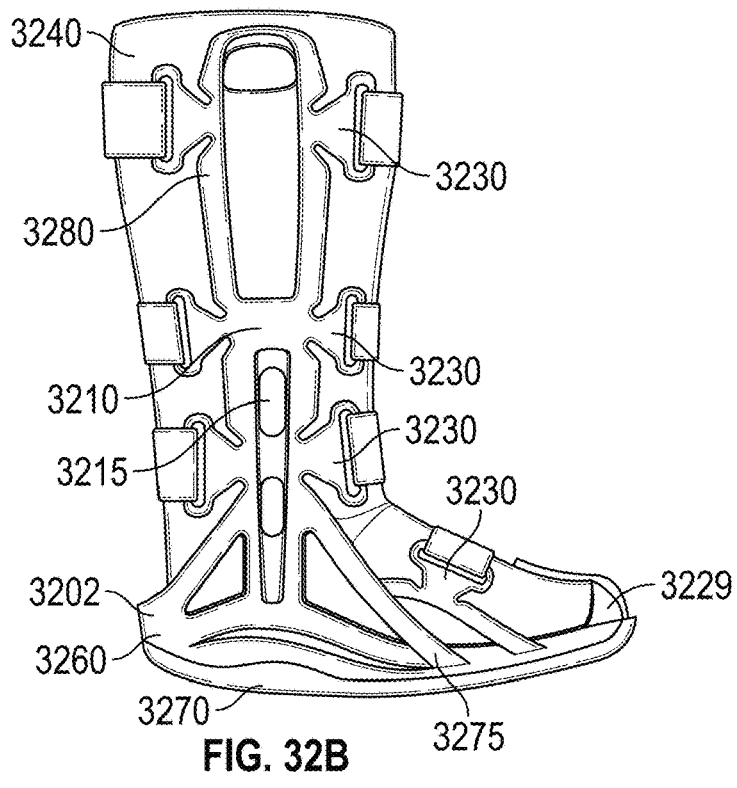
FIG. 32B illustrates a side view of the alternative walking brace of FIG. 32A, in accordance with some example embodiments.
Figure 32C:
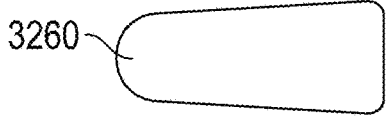
FIG. 32C illustrates a footbed profile of the alternative walking brace of FIGS. 32A and 32B, in accordance with some example embodiments.

FIGS. 32A-32C illustrate a second additional and/or alternative configuration for a walking brace, in accordance with some example embodiments. For example, FIG. 32A illustrates a perspective view of a walking brace 3200, in accordance with some example embodiments. FIG. 32B illustrates a side view of brace 3200 of FIG. 32A, in accordance with some example embodiments. And FIG. 32C illustrates a top view of a footbed 3260 profile of brace 3200 of FIG. 32A, in accordance with some example embodiments.

Walking brace 3200 comprises a continuous plastic, EVA or other suitable material that forms a footbed 3260, inner sole 3250, outer sole 3270 and an upright 3210 on either side of brace 3200 overmolded onto a semi-rigid metallic or plastic stay 3215 that spans the ankle portion of walking brace 3200, for example, rather than extending substantially an entire height of walking brace 3200. In some embodiments, outer sole 3270 is non-slip, comprising a tread pattern formed in the EVA foam. Alternatively, a non-slip tread can be adhered to outer sole 3270. Such a one-piece, continuous plastic overmold eliminates the need for typical riveting of formable aluminum upright bars to a rigid plastic boot foot-bed. Integration of metallic stay(s) 3215 with footbed 3260 and uprights 3210 allows walking forces on boot 3200 to be shared by the plastic of uprights 3210 and metallic stay(s) 3215. As illustrated in FIGS. 32A and 32B, the overmold material also forms a triangular or triangulated framing 3275 to further increase rigidity in the forward/backward direction, an integral toe cover 229 and an integral heel cover 3202, one or both covers providing "bump" protection. In some embodiments, toe cover 3229 and heel cover 3202 can be removed by cutting, unattaching and/or otherwise tearing one or both off.

Walking brace 3200 can further comprise upright extensions 3280, which may be similar to upright extensions 280, 380 as previously described. As illustrated, upright extension 3280, uprights 3210 and/or triangular frame 3275 can further comprise one or more flexible/rotatable chafes 3230, as described in connection with any chafe in this disclosure, or alternatively, molded-in D-rings that still retain sufficient flexibility to bend in a direction of tension exerted by one or more straps coupled thereto.

Walking brace 3200 comprises at least one upright strap 3220, configured to secure a lower leg of a user into brace 3200 and at least one lower strap, for example, a foot strap 3226 configured to wrap at least partly around and/or against a portion of the foot of the user. Straps 3220, 3226 are configured to coupled to chafes and/or molded-in D-rings 3230.

Brace 3200 may further comprise a liner 3240 comprising a soft, absorbent and, in some case, breathable, material configured to support and/or pad a foot and lower leg of a user. Liner 3240 can comprise any liner as previously described anywhere in this disclosure.

Figure 33A:
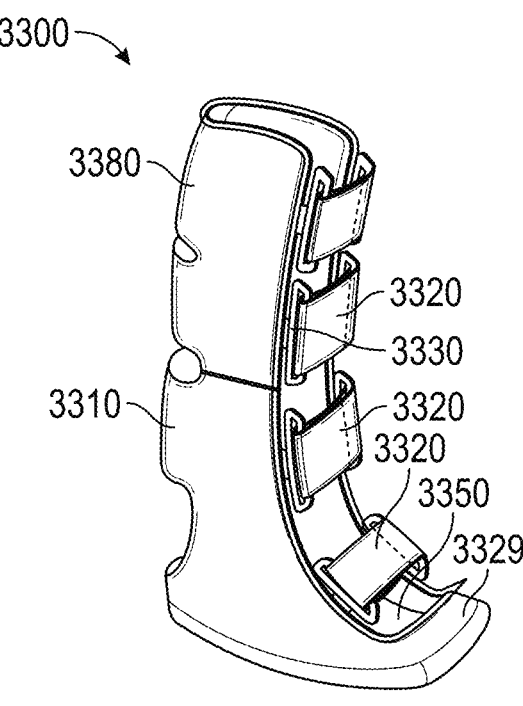
FIG. 33A illustrates a perspective view of yet another alternative walking brace, in accordance with some example embodiments.
Figure 33B:
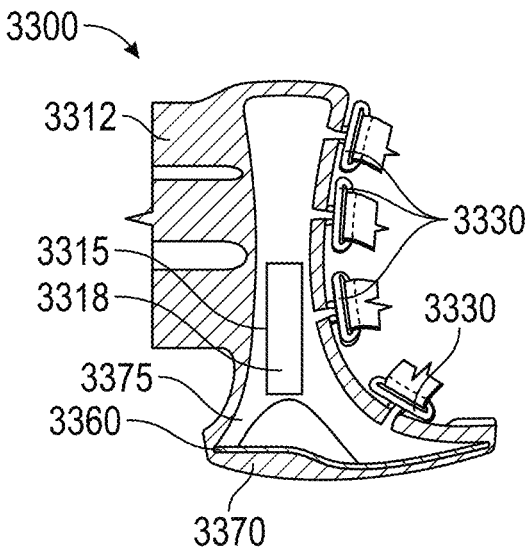
FIG. 33B illustrates a side cutaway view of the alternative walking brace of FIG. 33A, in accordance with some example embodiments.
Figure 33C:
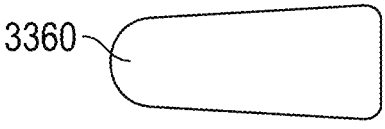
FIG. 33C illustrates a footbed profile of the alternative walking brace of FIGS. 33A and 33B, in accordance with some example embodiments.
Figure 34:
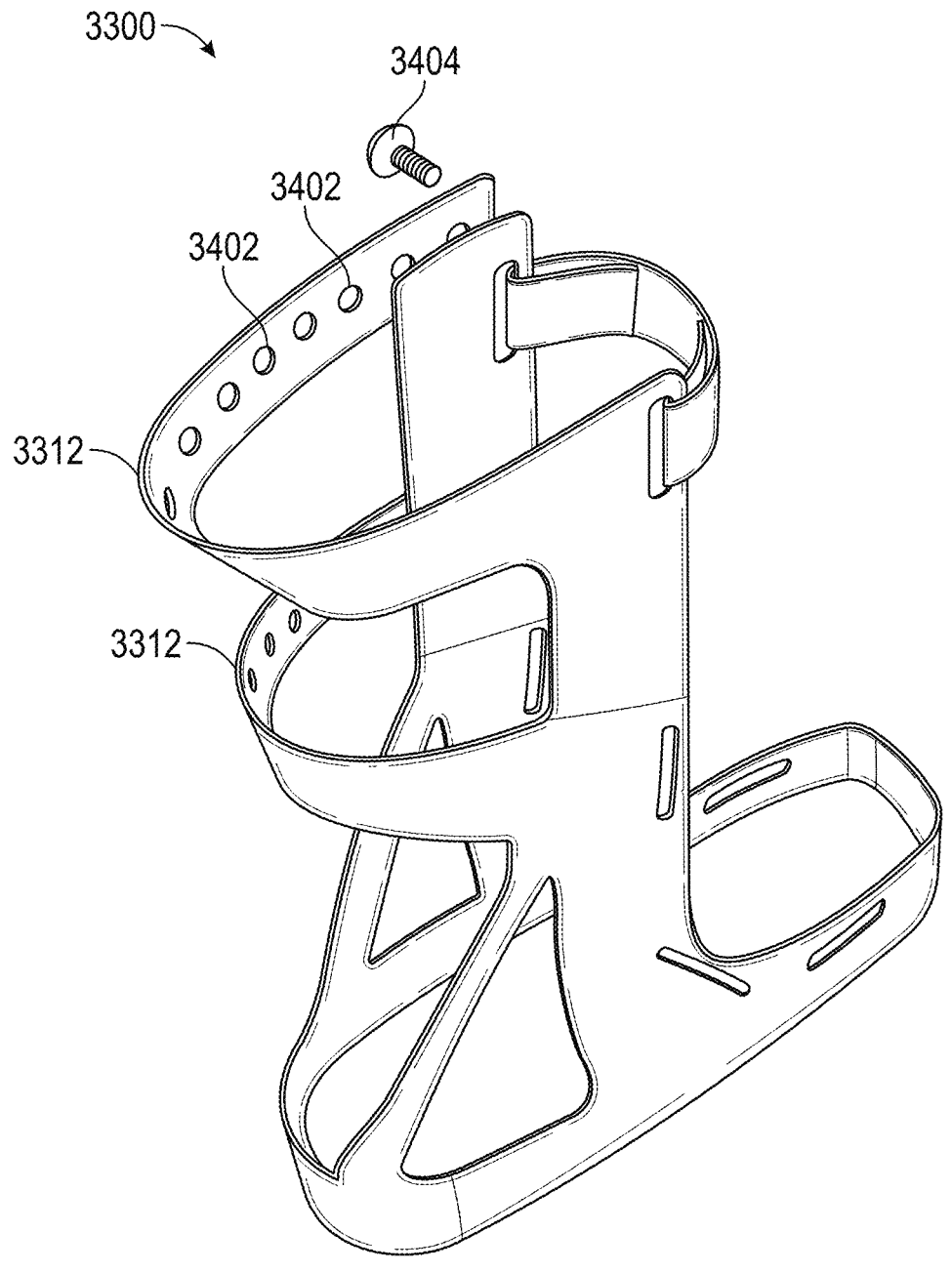
FIG. 34 illustrates a perspective view of one or more rear straps of a walking brace, in accordance with some example embodiments.

FIGS. 33A-33C and FIG. 34 illustrate a third additional and/or alternative configuration for a walking brace, in accordance with some example embodiments. For example, FIG. 33A illustrates a perspective view of a walking brace 3300, in accordance with some example embodiments. FIG. 33B illustrates a side cutaway view of brace 3300 of FIG. 33A, in accordance with some example embodiments. FIG. 33C illustrates a top view of a footbed 3360 profile of brace 3300 of FIG. 33A, in accordance with some example embodiments. And FIG. 34 illustrates a perspective view of one or more rear straps of walking brace 3300, in accordance with some example embodiments.

Walking brace 3300 comprises a continuous plastic, EVA or other suitable material that forms a footbed 3360, inner sole 3350, outer sole 3370 and an upright 3310 on either side of brace 3300 overmolded onto a semi-rigid metallic or plastic structure 3315 that extends substantially an entire height of walking brace 3300. In some embodiments, the overmold material further comprises an integral toe cover 3329 and an integral heel cover 3302, one or both covers providing "bump" protection. In some embodiments, toe cover 3329 and heel cover 3302 can be removed by cutting, unattaching and/or otherwise tearing one or both off. In some embodiments, outer sole 3370 is non-slip, comprising a tread pattern formed in the EVA foam. Alternatively, a non-slip tread can be adhered to outer sole 3370.

As illustrated, metallic and/or plastic structure 3315 includes a triangular frame 3375 disposed at an ankle region. Triangular frame 3375 may have substantially the same function as previously described triangular frame 3275. Metallic and/or plastic structure 3315 further comprises one or more molded-in D-rings that act as living hinges and retain sufficient flexibility to bend in a direction of tension exerted by one or more straps coupled thereto. Such a one-piece, continuous plastic overmold eliminates the need for typical riveting of formable aluminum upright bars or D-rings to a rigid plastic boot frame. Integration of metallic structure 3315 with footbed 3360 and uprights 3310 allows walking forces on boot 3300 to be shared by the plastic of uprights 3310 and metallic stay(s) 3315. As illustrated in FIGS. 33A and 33B, the metallic and/or plastic structure 3315 is further supported by a metallic insert 3318 disposed along the ankle region of brace 3300 and configured to increase rigidity in the forward/backward direction.

In some embodiments, brace 3300 further includes upright extensions 3380, which themselves may also include a portion of metallic and/or plastic structure 3315 that further comprises one or more molded-in D-rings that also act as living hinges and retain sufficient flexibility to bend in a direction of tension exerted by one or more straps coupled thereto. Advantageously, utilization of uprights 3380 or not provides brace 3300 with two heights. A lower, base height may utilize brace 3300 without upright extension(s) 3380, while a greater height can be had by utilizing upright extensions 3380. In some embodiments, upright extension (s) 3380 can be snapped into upright(s) 3310. However, the present disclosure is not so limited and any method of attachment between upright extensions 3380 and uprights 3310 is also contemplated.

Walking brace 3300 comprises a plurality of straps 3320, configured to couple to molded-in D-rings 3330 of one or both of uprights 3310 and upright extensions 3380, wrap around a front side of brace 3300 and secure a lower leg of a user into brace 3300. The overmold of uprights 3310 and/or of upright extensions 3380 further comprises at least one rear strap that is configured to wrap around a backside of the lower leg of the user and secure the lower leg of the user into the brace 3300 from the backside. In some embodiments, rear straps 3312 can comprise a fastener, for example a hook and loop fastener. In some embodiments, as further illustrated in FIG. 34, rear straps 3312 of brace 3300 comprise a plurality of holes 3402 configured to be stretched over a plastic "mushroom" shaped post 3404 secured to upright 3310 and/or to upright extension 3380 to thereby secure the lower leg of the user into the brace 3300 from the backside.

Implementations of the technology described herein are directed generally to a walking boot having a variety of unique features. To facilitate an understanding of the various embodiments described herein, a number of terms are further defined below.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range.

When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Any methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A method of manufacturing a walking brace, the method comprising:
   providing a U-shaped malleable stay that is configured to hold a manually-bent shape;
   overmolding an integral portion of the walking brace around the U-shaped malleable stay to form a footbed, a first upright disposed at a first side of the footbed and a second upright disposed on a second side of the footbed such that the U-shaped malleable stay extends through each of the footbed, the first upright and the second upright;
   forming a plurality of apertures in at least a portion of the walking brace; and
   providing a plurality of rotatable chafe assemblies, each comprising:
      a chafe comprising:
         a head having a slot for receiving a strap,
         a locking end portion, and
         a neck coupling the head to the locking end portion, the neck narrowing from the head to the locking end portion thereby allowing the neck to flex and extend in a direction of tension exerted by the strap; and
      a chafe lock comprising:
         a cap,
         a slot disposed under the cap, the slot configured to receive the locking end portion of the chafe, and
         a plurality of snap clips configured to rotatably secure the chafe lock in a respective one of the plurality of apertures and the locking end portion of the chafe in the slot of the chafe lock.

2. The method of claim 1, further comprising:
   providing a first upright extension configured to snap into a top portion of the first upright; and
   providing a second upright extension configured to snap into a top portion of the second upright, a first terminal end of the U-shaped malleable stay configured to insert into a first pocket of the first upright extension and a second terminal end of the U-shaped malleable stay configured to insert into a second pocket of the second upright extension.

3. The method of claim 2, further comprising:
   disposing hook and loop fasteners on at least one of an inward facing surface of one of the first and second upright extensions and an outward facing surface of one of the first and second upright extensions, each of the first and second upright extensions further comprising a first slot and a second slot; and
   providing at least one strap configured to pass through the first and second slots and to be secured to the hook and loop fasteners.

4. The method of claim 3, wherein the hook and loop fasteners are molded into the first and second upright extensions.

5. The method of claim 1, wherein the U-shaped malleable stay is metallic.

6. The method of claim 5, wherein the U-shaped malleable stay comprises aluminum.

7. The method of claim 1, further comprising providing a liner comprising:
   a fluid pump;
   a release valve;
   at least one inflatable cavity disposed within the liner and in fluid communication with the fluid pump and the release valve configured to adjust an inflation of the at least one inflatable cavity.

8. The method of claim 7, wherein the release valve comprises a release button and a protective rim having an edge that extends farther than an outside surface of the release button, thereby protecting the release button from accidental pressing.

9. The method of claim 1, wherein the U-shaped malleable stay comprises semi-rigid plastic.

10. The method of claim 1, wherein the U-shaped malleable stay comprises a pair of adjacently-disposed L-shaped malleable stays having a gap therebetween in the footbed.

11. The method of claim 1, wherein the first and second uprights each comprise a rear gusset that extends rearward at an angle from an upper portion of the upright to a lower portion of the upright.

12. The method of claim 1, further comprising:
   providing a toe cover;
   attaching at least one of:
      a first toe cover strap to the toe cover, the first toe cover strap configured to couple to at least one of a strap or a liner of the walking brace, and
      a second toe cover strap to the toe cover, the second toe cover strap configured to couple to at least one of an insole of the walking brace or the liner.

13. The method of claim 1, further comprising providing an insole comprising a plurality of raised portions and a plurality of air channels disposed between the plurality of raised portions, wherein a force exerted by a foot of a user on the insole deforms the plurality of raised portions and the plurality of air channels, thereby forcing air through the insole.

14. The method of claim 1, further comprising providing an insole comprising a removable Achilles heel portion that, when removed, provides access to a lower Achilles region of a foot of a user of the walking brace.

15. The method of claim 1, further comprising forming an under-boot sole comprising a heel-strike region having a greater thickness and increased strike-resistance compared to at least some other portions of the under-boot sole.

16. The method of claim 1, wherein the locking end portion of the chafe is a cylindrical feature having an ovoid or elliptical cross-section.

17. The method of claim 1, wherein the cap of the chafe lock is configured to directly contact at least a proximal portion of the respective one of the plurality of apertures and the snap clips are configured to snap around a backside of the respective one of the plurality of apertures.

\*  \*  \*  \*  \*